United States Patent
Ramanathan et al.

(10) Patent No.: US 8,725,241 B2
(45) Date of Patent: May 13, 2014

(54) VISUALIZATION OF PHYSIOLOGICAL DATA FOR VIRTUAL ELECTRODES

(75) Inventors: Charulatha Ramanathan, Solon, OH (US); Harold M. Wodlinger, Thornhill (CA); Ping Jia, Solon, OH (US); Harris Gasparakis, Lexington, MA (US); John E. Anderson, St. Louis, MO (US); Steven G. Arless, Baie Durfe (CA)

(73) Assignee: Cardioinsight Technologies, Inc., Cleveland, OH (US)

(*) Notice: Subject to any disclaimer, the term of this patent is extended or adjusted under 35 U.S.C. 154(b) by 396 days.

(21) Appl. No.: 13/128,136

(22) PCT Filed: Nov. 9, 2009

(86) PCT No.: PCT/US2009/063737
§ 371 (c)(1),
(2), (4) Date: May 6, 2011

(87) PCT Pub. No.: WO2010/054320
PCT Pub. Date: May 14, 2010

(65) Prior Publication Data
US 2011/0206256 A1    Aug. 25, 2011

Related U.S. Application Data

(60) Provisional application No. 61/112,494, filed on Nov. 7, 2008.

(51) Int. Cl.
*A61B 5/044* (2006.01)

(52) U.S. Cl.
USPC .......................................... 600/523; 600/525

(58) Field of Classification Search
USPC ................................................. 600/523, 525
See application file for complete search history.

(56) References Cited

U.S. PATENT DOCUMENTS

| | | |
|---|---|---|
| 3,954,098 A | 5/1976 | Dick et al. |
| 4,974,598 A | 12/1990 | John |
| 5,038,791 A | 8/1991 | Collins et al. |
| 5,054,496 A | 10/1991 | Wen et al. |
| 5,161,539 A | 11/1992 | Evans et al. |
| 5,390,110 A | 2/1995 | Cheney et al. |

(Continued)

OTHER PUBLICATIONS

Wang, et al., "Application of the Method of Fundamental Solutions to Potential-based Inverse Electrocardiography", Annals of Biomedical Engineering, vol. 34, No. 8, Aug. 2006 (2006 ©), pp. 1272-1288.

(Continued)

*Primary Examiner* — Chrsitopher D Koharski
*Assistant Examiner* — Michael Carey
(74) *Attorney, Agent, or Firm* — Tarolli, Sundheim, Covell & Tummino LLP

(57) ABSTRACT

Systems and methods can be utilized to visualize physiological data relative to a surface region (e.g., an organ) of a patient. A computer-implemented method can include storing electroanatomic data in memory representing electrical activity for a predetermined surface region of the patient and providing an interactive graphical representation of the predetermined surface region of the patient. A user input is received to define location data corresponding to a user-selected location for at least one virtual electrode on the graphical representation of the predetermined surface region of the patient. A visual representation of physiological data for the predetermined surface region of the patient is generated based on the location data and the electroanatomic data.

26 Claims, 12 Drawing Sheets

(56) References Cited

U.S. PATENT DOCUMENTS

| | | | |
|---|---|---|---|
| 5,480,422 | A | 1/1996 | Ben-Haim |
| 5,687,737 | A | 11/1997 | Branham et al. |
| 5,692,515 | A | 12/1997 | Rahn et al. |
| 5,697,377 | A | 12/1997 | Wittkampf |
| 5,713,946 | A | 2/1998 | Ben-Haim |
| 5,738,096 | A | 4/1998 | Ben-Haim |
| 5,803,084 | A | 9/1998 | Olson |
| 5,848,972 | A | 12/1998 | Triedman et al. |
| 5,891,049 | A | 4/1999 | Cyrus et al. |
| 6,016,439 | A | 1/2000 | Acker |
| 6,368,285 | B1 | 4/2002 | Osadchy et al. |
| 6,650,927 | B1 | 11/2003 | Keidar |
| 6,728,562 | B1 * | 4/2004 | Budd et al. ............ 600/374 |
| 6,782,287 | B2 | 8/2004 | Grzeszcuk et al. |
| 6,788,969 | B2 | 9/2004 | Dupree et al. |
| 6,920,350 | B2 | 7/2005 | Xue et al. |
| 7,016,719 | B2 | 3/2006 | Rudy et al. |
| 7,189,208 | B1 | 3/2007 | Beatty et al. |
| 7,266,408 | B2 | 9/2007 | Bojovic et al. |
| 7,286,866 | B2 | 10/2007 | Okerlund et al. |
| 8,224,432 | B2 * | 7/2012 | MacAdam et al. ............ 600/523 |
| 2004/0006268 | A1 | 1/2004 | Gilboa et al. |
| 2006/0149160 | A1 * | 7/2006 | Kofol et al. ............ 600/544 |
| 2007/0299351 | A1 | 12/2007 | Harlev et al. |
| 2008/0249424 | A1 | 10/2008 | Harlev et al. |

OTHER PUBLICATIONS

Burnes, et at, "A Field-Compatible Method for Interpolating Biopotentials", Annals of Biomedical Engineering, vol. 26, 1998, pp. 37-47.

Jia, of al., "Endocardial Mapping of Electrophysiolcgically Abnormal Substrates and Cardiac Anyhthmias Using a Noncontact Nonexpandable Catheter", Journal of Cardiovascular Electrophysiology, vol. 13, No. 9, Sep. 2002, Copyright © 2002 by Future Publishing Company, Inc., pp. 888-895.

Khoury, et al., "A Model Study of Volume Conductor Effects on Endocardial and Intracavitary Potentials", Department of Biomedical Engineering, Case Western Reserve University, Apr. 17, 1992, pp. 511-525.

* cited by examiner

VISUALIZATION OF PHYSIOLOGICAL DATA FOR VIRTUAL ELECTRODES

CROSS-REFERENCE TO RELATED APPLICATION

This application is a U.S. national stage entry under 35 U.S.C. 371 of International Application No. PCT/US2009/063737, which claims priority to claims benefit of U.S. Provisional Patent Application No. 61/112,494, which was filed on Nov. 7, 2008, and entitled VISUALIZATION OF PHYSIOLOGICAL DATA FOR VIRTUAL ELECTRODES. The entire contents of each of the above-identified applications is incorporated herein by reference.

TECHNICAL FIELD

The invention relates generally to systems and methods for visualizing physiological data for a surface region of a patient.

BACKGROUND

Various electrophysiology techniques have been developed for collecting electrophysiology data for a patient. Direct measurement techniques typically involve placing one or more electrodes into contact with biological tissue. For example, an electrophysiology catheter or probe contains one or more electrodes at its distal end, each electrode being able to record electrical activity at the location of said electrode. Thus, by placing the catheter at a particular location relative to a patient's organ, such as the heart, organ-specific electrical activity can be recorded. Signal processing, such as band-pass filtering, can be applied on any such signal to remove noise or otherwise enhance the recorded activity.

As a further example, catheters come in a variety of shapes and with a different number of electrodes (2, 4, 8 etc). Linear catheters are typically used to inspect the progression of the depolarization wave along the anatomy, and they are typically placed in well defined locations: The high right atrial (HRA) catheter monitors the progression of depolarization as it (typically) emanates from the sinoatrial (SA) node; the His catheter monitors progression of depolarization from the atria to the ventricles (typically through the His bundle); etc. A circular multipolar catheter may be placed proximal to or around a pulmonary vein to measure depolarization emanating from the pulmonary vein. Multi-electrode basket catheters may be placed in a chamber, and wholesale collect a plurality of data.

Electroanatomic electrophysiology mapping is a method by which acquired electrophysiology data is spatially depicted on a representation of an organ or body surface, which representation may be referred to as an "Electroanatomic Map". Examples of Electroanatomic Maps include the spatial depiction of cardiac activation time (also referred to as an isochrone map) or potential distribution on the cardiac surface, possibly as a function of time (potential map). Electroanatomic maps may also depict derived quantities, such as frequency domain analysis (e.g., dominant frequency distributions), cycle length maps, complex fractionated atrial electrogram (CFAE) distributions, regularity index distributions, as well as spatial correlation measures in either the time or frequency domain.

SUMMARY

The invention relates generally to systems and methods for visualizing physiological data for a surface region of a patient, such as a surface of an organ.

One aspect of the invention provides a computer-implemented method that includes storing electroanatomic data in memory representing electrical activity for a predetermined surface region of the patient and providing an interactive graphical representation of the predetermined surface region of the patient. A user input is received to define location data corresponding to a user-selected location for at least one virtual electrode on the graphical representation of the predetermined surface region of the patient. A visual representation of physiological data for the predetermined surface region of the patient is generated based on the location data and the electroanatomic data.

Another aspect of the invention provides a system for visualizing physiological data relative to an organ of a patient. The system includes electroanatomic data for the patient stored in memory. A patient geometry model is stored as patient geometry data in the memory. The patient geometry data representing at least one surface region of the organ of the patient. A location selector is programmed to generate location data in response to a user input corresponding to a user-selected virtual electrode location positioned relative to the patient geometry model. An output generator that generates a visual representation of physiological data for the virtual electrode that is determined as a function of the location data and the electroanatomic data.

DETAILED DESCRIPTION

Figure 1:
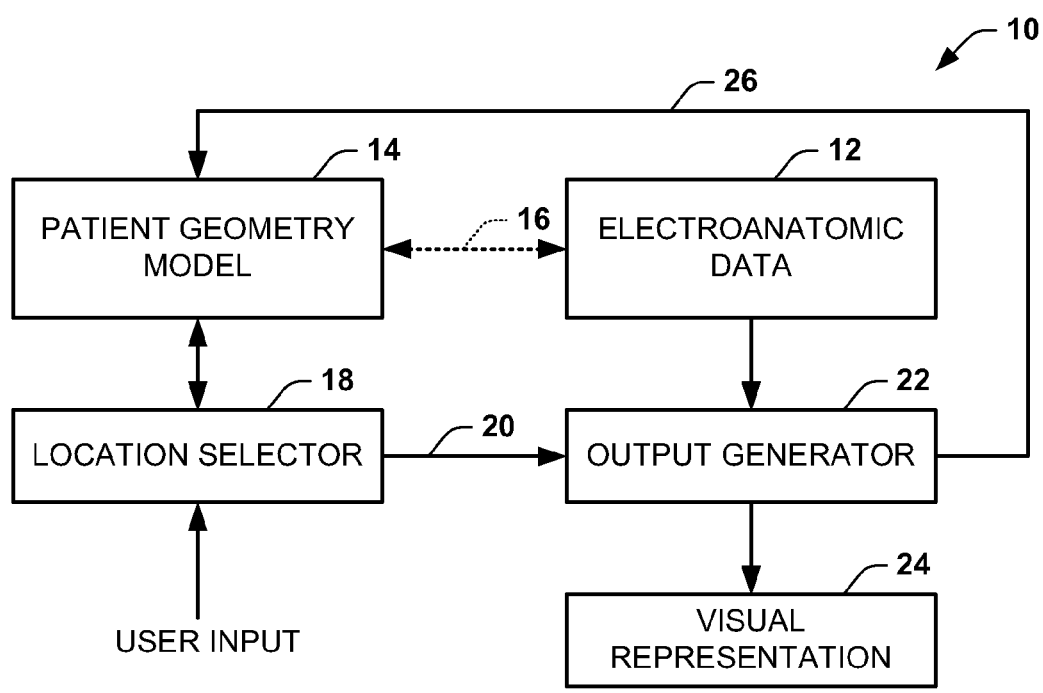
FIG. 1 depicts a block diagram of a system for visualizing physiological data in accordance with an aspect of the invention.

This invention relates generally to a system and method for visualization of electrical data for one or more virtual electrode. Electroanatomic data for a surface region of the patient is stored in memory. A user can select a location for one or more virtual electrode on a representation of a surface region of the patient (e.g., represented graphically as a surface model of an organ, such as the heart). A corresponding visual representation of physiological data for the surface region is generated based on the selected location and the electroanatomic data. The visual representation of physiological data can be generated in a separate window or superimposed on or be rendered near the representation of a surface region of the patient. For the example context of electrocardiographic imaging, the visual representation for each selected virtual electrode location can be in the form of one or more of a voltage potential, power spectrum (amplitude vs. frequency), unipolar electrograms, bipolar electrograms, statistical information, cycle length, synchrony index, conduction velocity or the like.

As used herein, the term "virtual" in the context of electrodes or other selected anatomical locations means that the selected location or structure is not a physical electrode construction, but instead is parameterized by data (e.g., as mathematical model) at a point, a collection of points or a surface region that is selected by a user. The resulting visual representation of the physiological data for a given virtual electrode thus can represent electrophysiology data that has been acquired, that has been computed or a combination of acquired and computed data for a set of one or more geometrical points associated with a surface region of the patient.

Those skilled in the art will appreciate that portions of the invention may be embodied as a method, data processing system, or computer program product. Accordingly, these portions of the invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention are described herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processors of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus (see, e.g., FIG. 13) to cause a series of operational steps to be performed on the computer or other programmable apparatus to produce a computer implemented process such that the instructions which execute on the computer or other programmable apparatus provide steps for implementing the functions specified in the flowchart block or blocks.

FIG. 1 depicts an example of a system 10 for visualizing physiological data of a patient. The system 10 can be implemented in a standalone computer, a workstation, an application specific machine, or in a network environment in which one or more of the modules or data can reside locally or remotely relative to where a user interacts with the system 10.

The system 10 employs electroanatomic data 12 for a patient, such as can be stored in an associated memory device (e.g., locally or remotely). For instance, the electroanatomic data 12 can represent electrical information for a plurality of points, each of which is indexed or otherwise associated with an anatomical geometry of the patient, such as can be embodied as a patient geometry model 14. In one embodiment, the patient geometry model can be a surface of model of a patient's organ, such as the heart, which can be graphically rendered a two- or three-dimensional representation.

The patient electroanatomic data 12 can be raw data, such as has been collected from an electrophysiology mapping catheter or other means that can be utilized to gather electrophysiology data for a selected region of a patient (e.g., of an organ, such as the heart). Additionally or alternatively, the electroanatomic data 12 can correspond to processed data, such as can be computed from raw data to provide electrophysiology information for the selected region of the patient (e.g., a surface of an organ, such as the heart).

By way of example, a contact or non-contact electrophysiology catheter can be placed in a patient's heart and collect electrophysiology data at a plurality of spatial locations over time, such as during a number of one or more cardiac intervals. Such data can be spatially and temporally aggregated in conjunction with image data for the patient's heart to provide the electroanatomic data 12 for the patient's heart. Alternatively, other devices (e.g., catheters or patches) can be placed on or near a patient's heart, endocardially and/or epicardially, such as during open chest and minimally invasive procedures, to record electrical activity data, which can be mapped to a representation of the patient's heart to provide similar corresponding electroanatomic data.

As another example, non-invasive electrophysiological mapping (e.g., electrocardiographic imaging for the heart) can be performed on the patient to generate the electroanatomic surface data 12. This technique can generate electrophysiological data by combining body surface electrical measurements with patient geometry information through an inverse method programmed to reconstruct the electrical activity for a predetermined surface region of the patient's organ. Thus the results of the inverse method can provide the corresponding electroanatomic data 12 that is registered with (or indexed) relative to patient geometry model 14.

Those skilled in the art will understand and appreciate that the system 10 is equally applicable to patient electroanatomic data 12 that can be gathered and/or derived by any of these or other approaches, which may be invasive or non-invasive. Additionally, it will be understood and appreciated that the electroanatomic data 12 can be provided in any form and converted into an appropriate form for processing in the system 10.

In addition to the patient electroanatomic data 12 related to the patient's organ, the system 10 also employs a patient geometry model 14, such as can represent a predetermined surface region of an anatomical structure. For example, the patient geometry model 14 can correspond to a patient-specific representation of a surface of an organ or other structure to which the patient electroanatomical data has been registered. For instance, the patient geometry model 14 may be in the form of a graphical representation of a region of the patient's organ, such as can be generated by appropriate imaging processing of image data acquired for the patient. Such image processing can include extraction and segmentation of an organ from a digital image set. The segmented image data thus can be converted into a two-dimensional or three-dimensional graphical representation of a surface region of the patient's organ. Alternatively, the patient geometry model 14 can correspond to a mathematical model of the patient's organ that has been constructed based on image data for the patient's organ. Appropriate anatomical or other landmarks can be associated with the organ represented by the anatomical data for the organ to facilitate subsequent processing and visualization in the system 10.

As mentioned above, the electroanatomic data 12 can be registered into a common coordinate system with the patient geometry model 14. For instance, the electroanatomic data 12 can be stored in a data structure of rows (corresponding to different anatomical points) and columns (corresponding to samples) in which the rows of data have the same index as (or are registered to) respective points residing on patient geometry model 14. This registration or indexed relationship between the electrical data 12 and the patient geometry model 14 is indicated by a dashed line at 16. In one embodiment the samples in each of the columns can represent simultaneous information across the entire surface region (e.g., the heart) of the patient.

The patient geometry model 14 can be generated from image data that is acquired using nearly any imaging modality. Examples of imaging modalities include ultrasound, computed tomography (CT), 3D Rotational angiography (3DRA), magnetic resonance imaging (MRI), x-ray, positron emission tomography (PET), and the like. Such imaging can be performed separately (e.g., before or after the measurements) utilized to generate the electroanatomic data 12. Alternatively, imaging may be performed concurrently with recording the electrical activity that is utilized to generate the patient electroanatomic data 12 or the imaging. It will be understood and appreciated by those skilled in the art that the system 10 is equally applicable to employ anatomical data that may be acquired by any one of these or other imaging modalities.

Alternatively or additionally, the patient geometry model 14 can correspond to a generic or custom representation of an organ, which may not be the patient's own organ. In such a case, the electroanatomic data 12 can be mapped (via registration 16) to the representation of the organ according to identified anatomical landmarks. A manual, semi-automatic or automatic registration process can be employed in order to register the anatomical model with the signal acquisition system, if any.

It further will be understood and appreciated that depending upon the format and type of input data appropriate formatting and conversion to a corresponding type of representation can be implemented by the system 10. For instance, the patient electrical data 16 and anatomical data 18 can be provided to the system 10 in a known format or be converted to a standard format for processing by the system. As a further example, the electrical data 16 and the anatomical data 18 can be combined to provide an aggregate set of electroanatomical data for the patient.

The system 10 also includes a location selector 18 that is programmed to select a location on a graphical representation of the patient geometry model 14. The selected location is translated to location data 20. The location data 20 can correspond to a three-dimensional position in a coordinate system that is associated with the patient geometry model 14. As an example, a user can employ a cursor via a pointing device (e.g., a mouse) to identify and select a location on the two-dimensional graphical representation of the patient geometry model 14. The 2-D screen location can be translated to a corresponding 3-D position on the model 14 according to the selected location.

An output generator 22 is programmed to generate a visual representation 24 of physiological data based on the location data 20 and the electroanatomic data 12. If the selected location does not correspond exactly to location at which physiological data had been acquired or derived for the electroanatomic data, the output generator can locate a nearest point (or points) from which the desired physiological data can be determined.

The output generator 22 can be programmed to provide a variety of different types and formats of physiological information. For example, the information can be in the form of graphs, text or numerical values, which can be provided in separate windows adjacent to the graphical representation of the patient geometry model 14. Additionally or alternatively, the output generator 22 can provide a visual representation (e.g., in the form of a graph or numerical value that is rendered as an object graphically superimposed relative to the graphical representation of the patient geometry model 14, indicated by arrow 26.

The output generator 22 can be programmed to provide any number of one or more visual representations 24 of physiological data such as in response to a user selecting one or more virtual electrode locations on the patient geometry model 14. In one operating mode (referred to herein as a roving virtual electrode mode or a roving mode) the output generator 22 can provide the visual representation 24 (e.g., in the form of an electrogram or power spectrum or otherwise) that is superimposed on the graphical representation of the geometry model 14 at or near the current location of the cursor. For example, as a user moves the cursor relative to the representation of the surface model 14 on the display, a corresponding visual representation for the virtual electrode is continuously displayed at or near the current cursor location. Thus, the information presented in a visual representation for a roving virtual electrode changes as a function of the position of the cursor on the anatomical model 14. The output generator 22 can also include controls to allow a user to pin or fix the corresponding visual representation at a desired current location through activation of a suitable user interface element (e.g., context menu or the like).

Figure 2:
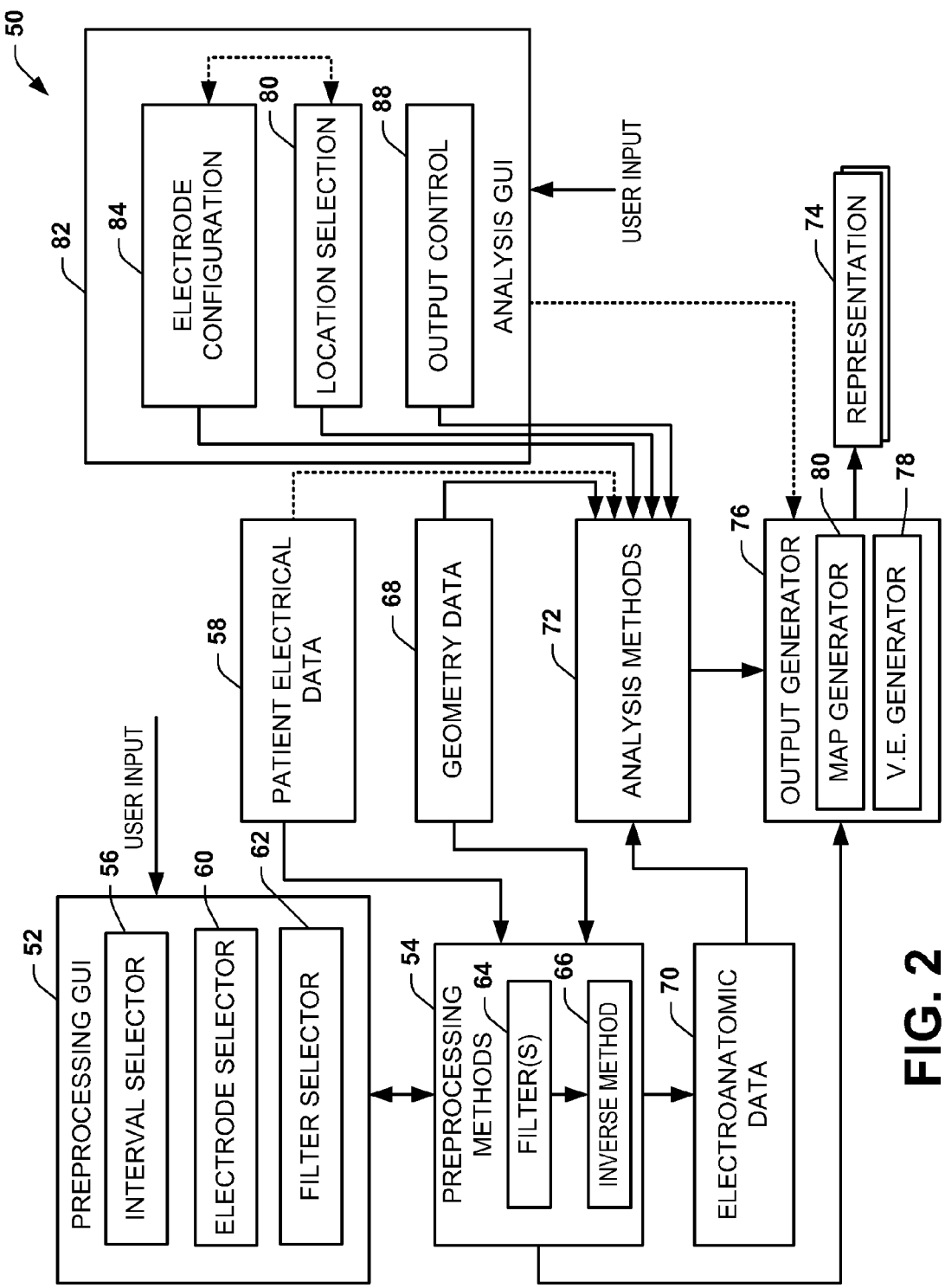
FIG. 2 depicts a block diagram of a system for visualizing physiological data for one or more virtual electrodes in accordance with another aspect of the invention.

FIG. 2 depicts an example of another system 50 for visualizing physiological data for a patient. In the example of FIG. 2, features of the system 50 for performing preprocessing as well as analysis and generation of visual representations are depicted. The preprocessing portions of the system 50 can be utilized to preprocess and convert the data to an appropriate form for an appropriate time interval such as can include one or more beats. The system 50 includes a preprocessing graphical user interface (GUI) 52 that is responsive to user inputs. The preprocessing GUI 52 can include a plurality of selection mechanisms each of which can activate corresponding preprocessing methods 54.

In the example of FIG. 2, the preprocessing GUI 52 includes an interval selector 56 that can be utilized to select one or more time intervals that may be of interest to the user. For example of electrocardiographic analysis, the intervals can correspond to beats or cardiac cycles any user defined time interval (e.g., a portion of one or more cycles) over which electrical data 58 has been acquired.

As described herein with respect to FIG. 1, the patient electrical data can be acquired by various techniques, including invasive as well as non-invasive approaches. Thus, the patient electrical data 58 can correspond to substantially raw data that has been acquired for the patient, such as representing signals acquired for each of a plurality of electrodes.

The preprocessing GUI 52 can also include an electrode selector 60 that is utilized to select which electrode or electrodes are to be utilized to populate an output result set for use in further processing and analysis. The electrode selection can be automated, manual or a combination of manual and automated. The electrode selector 60 can be provided via a GUI that allows a user to selectively enable or disable each of the plurality of electrodes that have been utilized to acquire patient electrical data at a corresponding anatomic location. As an example, a plurality of electrodes can be distributed over a patient's torso for acquiring electrical information during a sampling period. Thus, the electrode selector can be employed to set which sensor or sensors will be utilized to acquire and define the subset of the patient electrical data 58. Automated methods can also be utilized to detect and remove bad channels.

The preprocessing GUI 52 can also include a filter selector 62 that can be utilized to select one or more preprocessing filters 64 for the selected set of patient electrical data 58. The preprocessing filters, for example, can include software methods programmed to filter the electrical data 58, such as including a low pass filter, DC removal filter, a de-trending filter, or a Wilson Central Terminal (WCT) filter. Those skilled in the art will understand and appreciate other types of filters 64 that can be selectively activated or deactivated via the filter selector 62.

As the filters are turned on or off or otherwise adjusted (parametrically), the filter methods 64 can be applied to the electrical data 58 and generate a corresponding filtered set of the patient electrical data (as also may be reduced according to the selected interval(s) and the electrodes that has been selected). After the filtering, electrode/channel selection and time interval selection have been implemented, the preprocessing GUI 52 (or other means or activation) can be utilized to activate an inverse method 66, such as described herein. The inverse method 66 utilizes geometry data 68 along with the modified patient electrode data (for the selected time interval, selected channels and filtered) to generate corresponding electrical anatomic surface data 70. The electroanatomic data 70 is indexed or registered relative to predefined surface region of a patient, such as an epicardial surface or an endocardial surface of a patient's heart.

Examples of inverse methods suitable for use with body surface electrodes are disclosed in U.S. Pat. No. 6,772,004, entitled System and Method for Non-invasive Electrocardiographic Imaging and U.S. patent application Ser. No. 11/996,441, (now U.S. Pat. No. 7,983,743) entitled System and Method for Non-invasive Electrocardiographic Imaging, both of which are incorporated herein by reference. It will be appreciated that other approaches can be utilized to generate the electroanatomic data, which further may vary according to the mechanism utilized to acquire the patient electrical data 58.

Figure 3:
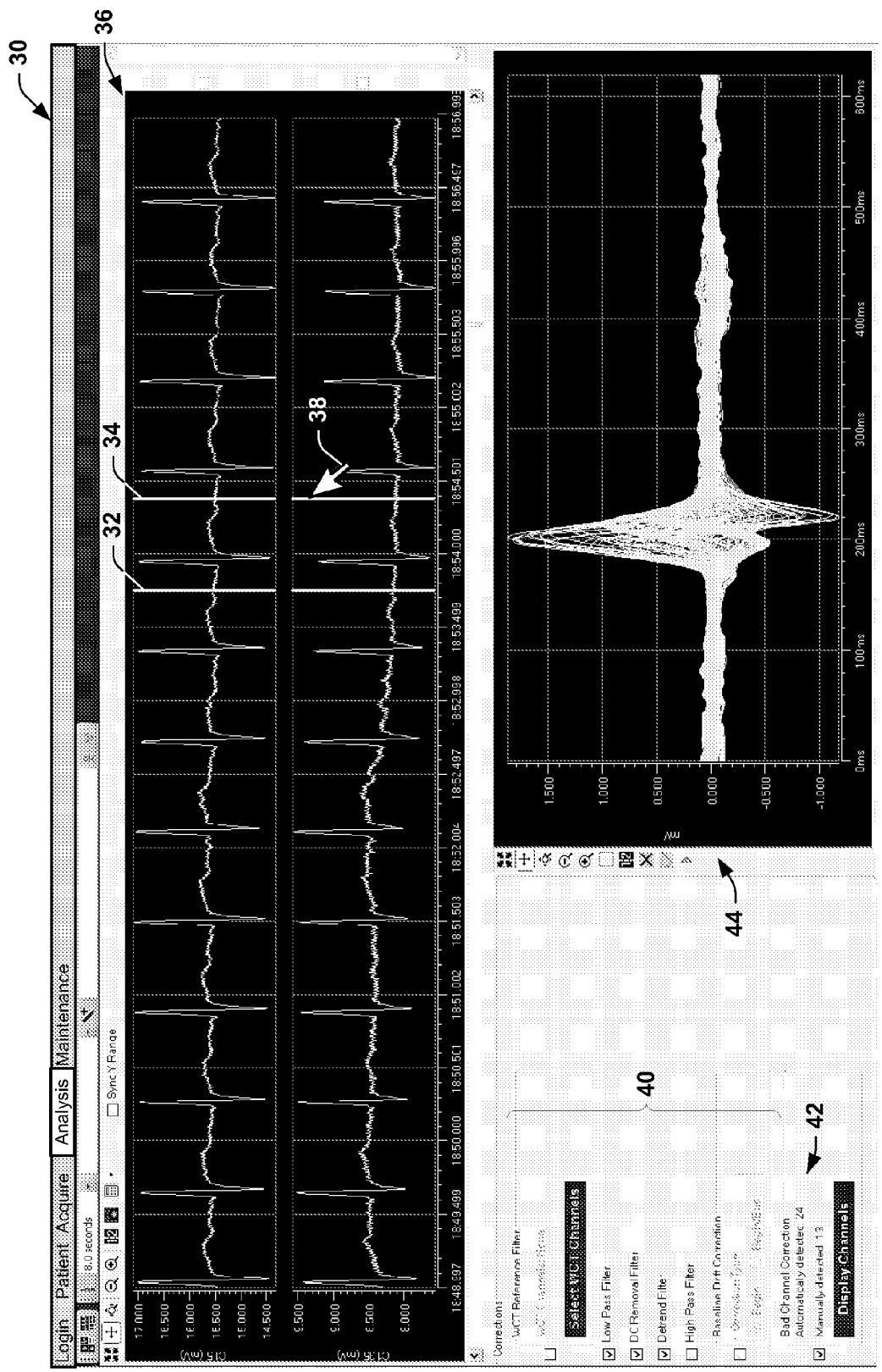
FIG. 3 depicts an example of a GUI that can be implemented for use in conjunction with performing preprocessing in a visualization system according to an aspect of the invention.

FIG. 3 depicts an example of a portion of a pre-processing GUI 30 that can be implemented for the system 50 of FIG. 2. The preprocessing GUI 30 includes interval selection and filter selection GUI elements. In the example of FIG. 3, an interval is shown by calipers 32 and 34 in the waveform window 36. While two waveforms are illustrated in the window 36 in this example, those skilled in the art will appreciate and understand that any number of such waveforms can be depicted in the GUI 30 and that the number of waveforms can be selected by the user. The interval calipers 32 and 34 can be initially positioned at a given location in the waveform window 36, such as in response to activating an interval selection user interface element. A user can adjust the caliper positions via a cursor (or other pointing element) 38. Thus, by adjusting the distance between the respective calipers 32 and 34 a desired interval or beat can be selected by the user for further processing as described herein. While a single interval is illustrated in FIG. 3 by calipers 32 and 34, it is to be understood and appreciated that any number of one or more such intervals can be selected, for additional types of processing.

Also depicted in FIG. 3 are filter selection GUI elements 40, such as corresponding to the filter selector 62 of FIG. 2. In the example of FIG. 3, various types of corrections and filtering can be selectively performed on patient electrical data, including are the WCT reference filter, low pass filtering, DC removal filter, de-trending filter, a high pass filter and baseline drift correction.

Additionally, bad channel correction may be implemented via GUI elements 42, such as if data appears outside of expected operating parameters. The bad channel correction GUI elements 42 can be activated to implement an automatic method that detects and selects waveforms determined to correspond to bad channels (or bad electrodes). Additionally, waveforms can be selected manually from the corresponding graphical waveform window 44 if they appear anomalous relative to the other waveforms. Those skilled in the art will appreciate various approaches that can be implemented to remove the anomalies or bad channels can be removed from the sensor data.

Returning to FIG. 2, the visualization system 50 also includes analysis methods 72 that are programmed to provide results data for generating a representation 74 of physiological data relating to the patient's organ. The representation 74 can be generated based the electroanatomic data 70 for the patient. The representation 74 may include graphics, text information, or a combination of graphics and text. It will be appreciated that the representation 74 provided by the system 50 is not limited to quantities actually measured or otherwise provided in the electroanatomic data 70, but can also correspond to electrophysiology data for a one or more virtual electrodes as may be selectively positioned by a user.

The analysis methods 72 can provide results data to an output generator 76 based on parameters established by a user, or preconfigured either by physician preferences possibly per procedure type. The output generator 76 is programmed to provide the representation(s) 74 in one or more forms, which can vary depending on the type of data being displayed.

As one example, the output generator 76 includes a virtual electrode (VE) generator 78 for providing the visual representation 74 responsive to a user selecting one or more locations in a predetermined surface region of a patient. Each selected location can correspond to a location in a coordinate system that can be defined or represented by the geometry data 68. For instance by selecting a location in a patient geometry coordinate system, corresponding electrical information in the electroanatomic data 70 for the nearest geometrical point (or a collection of nearest points) can be utilized by the analysis methods 72 to provide the results. The virtual electrode generator 78 in turn generates the corresponding representation of physiological data from the results of the analysis.

The representations 74 provided by the virtual electrode generator 78 can be considered spatially localized in response to a user selection, such as for providing data at a selected point (in the case of each single point virtual electrode) as well as along a plurality of user-selected locations corresponding to a multi-point or multi-dimensional virtual electrode. The representation of physiological data 74 generated for each virtual electrode can be in the form of graph, text/numerical information or a combination of graphs and text/numerical information. Any number of one or more representations can be generated for each virtual electrode.

The output generator 76 also includes a map generator 80 that is programmed for generating physiological data in the form of an electroanatomic map that is superimposed over the predetermined surface region of the patient's organ. For example, the map generator 80 can render one or more maps over the entire surface representation of the patient's organ, such as can be a two-dimensional or three-dimensional representation thereof. For instance, the map generator 80 can be programmable in response to a user-selection (e.g., via drop down context menu) to select which type of electroanatomic map will be generated.

The output generator 76 can provide the representation 74 as including information similar to that which might be generated based on electroanatomic data 70 provided according to any of the mechanisms described herein, including temporal and spatial characteristics that can be determined from acquired patient electrical data. As described herein, however, the system 50 enables the user to define a configuration of one or more virtual electrodes of a defined type and a location of such catheter(s) relative to the organ for which the representation 74 will be generated.

Additionally or alternatively, the configuration and placement of the virtual electrodes can be automatically selected by the analysis methods 72, such as to place an arrangement of one or more virtual electrodes at desired anatomic locations (e.g., landmarks), which can be defined by user-defined parameters. The user can also set parameters and properties to define what type of output or outputs the representation 74 will include. Thus, once the electrophysiology data has been acquired for a patient (using any technique) and stored in memory as the electroanatomic data 70, a user can employ the system 50 to virtualize physiological data of interest for the patient's organ. These results can be accomplished without requiring the user of the system 50 to actually acquire any new electrophysiology data from the patient. Thus, the system 50 can be a powerful addition to existing electrophysiology systems as well as can be utilized as a standalone system.

The system 50 includes an analysis user interface GUI 82 that is programmed to provide a human-machine interface for controlling and activating the analysis methods 72. A user can employ the GUI 82 via a user input device (e.g., a mouse, keyboard, touch screen or the like) to enter user inputs to set parameters and variables as well as to control display techniques and algorithms utilized by the analysis methods 72.

The user interface 82 can include a configuration component 84 that is utilized to define a configuration and arrangement of one or more electrodes for which one or more of the resulting representations 74 will be constructed. For example, the configuration component 84 can provide the user with an electrode configuration data set that includes a plurality of predefined electrode types. The predefined electrode configurations can correspond to any number of one or more electrophysiology catheters, which may correspond to commercially available products. For example, the predefined electrode configurations can correspond to any number of one or more electrode configurations that have been previously defined or constructed by a user or otherwise stored in memory as a library of available virtual electrode configurations. As described herein, the available electrode configurations can range from a single electrode (corresponding to a single point) or a linear arrangement of electrodes (such as disposed along a catheter or probe), two-dimensional (e.g., a patch or surface configuration) or three-dimensional electrode configurations (e.g., representing a volumetric arrangement of electrodes). These and other virtual electrode structures can be defined via the electrode configuration component 84. A user can also specify the number of electrodes and spatial distribution of such electrodes for a given configuration. As an example, a single electrode may be defined as a default setting for a virtual electrode, which can be modified to a different configuration via the configuration GUI 84.

The user interface 82 also includes a location selection component 86. The location selection component 86 can be utilized to identify one or more locations at which the selected electrode configuration (e.g., comprising one or more electrodes) is to be positioned relative to the patient's organ. For example, the location selection component 86 can employ a GUI element, such as a cursor, that a user can position with a pointing device (e.g., a mouse, touch screen and the like) to select a corresponding anatomical location on a graphical depiction of the patient's geometry. For example, the location can be on a selected surface region of an organ, in the organ or proximal to the organ. As described above, the representation 74 can be generated for the selected location based on the location data, electroanatomic data 70 for a given virtual electrode configuration.

As an example, in response to the user input, the location selection component 86 can cause a graphical representation of the selected electrode configuration (e.g., a single virtual electrode or an arrangement virtual electrodes, such as in the form of a catheter, a patch or other type electrophysiology measuring device) to be positioned at the selected location. The location selection component 86 can also be utilized to adjust the orientation (e.g., rotate) and position of the selected electrode structure relative to a two-dimensional or three-dimensional coordinate system for an anatomical model of the patient's organ. That is, as described herein, the selected location of a cursor on an image can be translated to a position (e.g., in a three dimensional coordinate system) relative to known patient geometry. Additionally or alternatively, the location selection component 86 can provide a list of one or more predefined common anatomical locations. The common locations can be programmable and include user-defined locations as well as those known in the art to be useful locations for visualizing electrical activity for the organ.

As a further example, in situations where a user is to define the virtual electrode configuration as a catheter having a single electrode or having a plurality of electrodes, the location selection component 86 can be utilized to identify a location at which the catheter is to be positioned. In response to the user identifying the location, the identified location can be populated with a graphical representation of the virtual electrode structure superimposed over the graphical representation of the interactive surface region of patient anatomy.

Additionally or alternatively, the cursor itself can also take on the form of the selected virtual electrode construct, such as while it moves across a window in which the organ model is being displayed.

In addition to selecting a desired location at which a virtual electrode is to be positioned, the location selection GUI 86 can provide means for a user to draw a contour or a closed surface at a desired location on the graphical representation of the patient's organ (e.g., on the left ventricle of the heart). The resulting contour or closed surface can identify a corresponding path or boundary for a virtual electrode structure. For a contour, the length of the contour can be automatically populated with an arrangement of virtual electrodes. Similarly, an interior of the patch boundary can be automatically populated with an arrangement of electrodes. The spatial distribution and number of electrodes can be specified by the user (via the electrode configuration component 84). The arrangement and spatial distribution of electrodes for a given configuration can be uniform (e.g., as a default setting) or it may be non-uniform, as programmed by a user.

The user interface 82 can also include an output control component 88 that is utilized to set output parameters and properties for each representation 74 that is generated. The output control component 88 can be utilized to select one or more measured or derived electrophysiology parameters that can be provided as part of the representation 74 based on the electrode configuration data and location data for each virtual electrode electrode configuration. The output control 88 can be programmed to provide the employ the same algorithm for each virtual electrode or, alternatively, different algorithms or constraints can be defined for each virtual electrode. The results set for the selected output control can include electrical potentials (e.g., unipolar or bipolar electrograms, activation times, frequency information (e.g., power spectrum), and statistics relating to these as well other derived quantities.

Another application of the output control component 88 can be to selectively swap electrode configurations for comparative purposes. For example, the output control component 88, individually or in combination with the electrode configuration component 84, can be employed to add or remove as well as to reposition two or more selected catheters relative to the representation of the patient's organ to modify the results provided in the output representation 74.

The output control 88 further may be utilized to implement comparative functions between algorithms, between temporal sets of different electrophysiology data or to otherwise constrain the resulting output data that is to be visualized on the output device.

By way of example, the output representation 74 may include the statistics of activation within a region of the patient's organ (e.g., as defined by placement of a 2-D virtual electrode or a virtual patch), including a minimum, a maximum, an average, and a standard deviation of activation time, a minimum, maximum, average and a standard deviation of the electrical potential. Those skilled in the art will appreciate that other statistical analyses or properties may be part of or derived from the electroanatomical data 70.

As a further example, the output control 88 can be utilized to control or establish a filter that controls what information will be utilized by the analysis methods 72 to generate a corresponding output representation 74. For instance, a user can employ the output control 88 to set an interval for ascertaining activation time or other constraints for each virtual electrode. As another example, an interval can be set by a user that is utilized to determine a dominant frequency for each virtual electrode. A corresponding dominant frequency map can also be generated. Thus based on such constraints, locations (corresponding to anatomical positions) that satisfy such time limits or other constraints can be determined and provided to the output device for display graphically (or otherwise) on a graphical representation of the organ. It will be thus appreciated that any type of data that can be measured or computed for an electrode arrangement positioned relative to a patient's organ can be computed and be provided in a virtual environment based on electroanatomic data 70.

Figure 4:
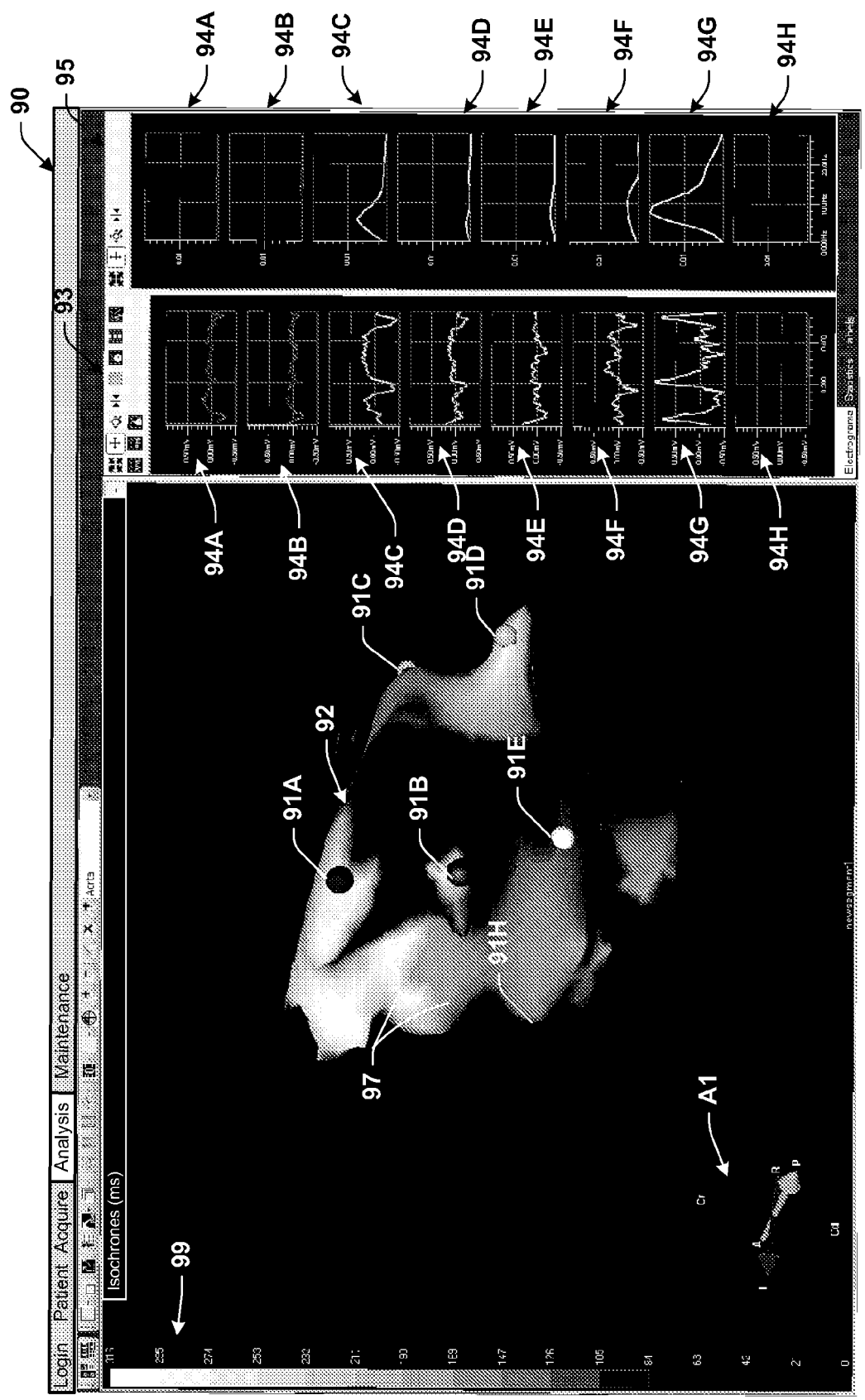
FIG. 4 depicts an example of a graphical user interface for a visualization system that employs virtual electrodes in accordance with an aspect of the invention.

FIG. 4 depicts an example of a GUI 90 in which a plurality of virtual electrodes 91A, 91B, 91C, 91D, 91E, 91F, 91G and 91H have been positioned at user-selected locations on the graphical representation of a surface of a patient's heart 92. It will be appreciated that, as described herein, any number of virtual electrodes can be positioned on the surface. Adjacent to the window in which the surface representation 92 is depicted, are additional analysis and evaluation tools.

In the example of FIG. 4, an electrogram window 93 is populated with an electrogram 94A, 94B, 94C, 94D, 94E, 94F, 94G and 94H for each of the virtual electrodes 91A, 91B, 91C, 91D, 91E, 91F, 91G and 91H, respectively. Thus, each electrogram displays the electrical activity (voltage versus time) according to the electroanatomical data determined for each point at which the respective virtual electrodes are positioned.

Additionally depicted in FIG. 4 is a window 95 that includes power spectrums graphs 96A, 96B, 96C, 96D, 96E, 96F, 96G and 96H for each of the virtual electrodes 91A, 91B, 91C, 91D, 91E, 91F, 91G and 91H. Power spectrum demonstrates frequency versus amplitude, such as can be computed from the electrograms 94A, 94B, 94C, 94D, 94E, 94F, 94G and 94H associated with each of the respective virtual electrodes 91A, 91B, 91C, 91D, 91E, 91F, 91G and 91H.

Additionally in the example of FIG. 4, a coordinate axis Al is depicted adjacent to the surface model demonstrating the relative orientation of the patient's heart model 92. A user can further rotate the three-dimensional surface model 92 (e.g., via the cursor or other image controls) to a desired orientation for selecting and applying virtual electrodes to one or more selected surface region.

FIG. 4 also depicts an example of an isochrone map 97 superimposed on heart model 92. The isochrone map 97 depicts activation times that have been computed as a function of an interval selected (via GUI element or button) in the electrogram window 94. Similar to the interval selection shown and described in FIG. 3, a user can employ the cursor to selectively adjust calipers 98 to adjust an interval in the displayed electrograms. As the calipers 98 are adjusted, a corresponding activation time can be computed and contemporaneously displayed in the isochrone map. A graphical scale (or key) 99 can be provided adjacent to the isochrone map 97 to inform the user of what each shade or color in the map represents.

By way of example, the activation time can be computed by analyzing the change in voltage over time (e.g., dV/dt) within the selected time interval. Alternatively, such as depending upon the type of waveform, wavelet analysis can be performed to ascertain the activation time for a given waveform. The corresponding activation times are rendered as a graphical representation that is superimposed on the patient's heart model. A corresponding color code or gray scale can be provided to enable the user to determine the activation time for each portion of the patient's heart. A user further may actively modify the time interval with resulting in corresponding changes to the activation time being displayed in the activation map that is superimposed on the patient's heart.

Figure 5:
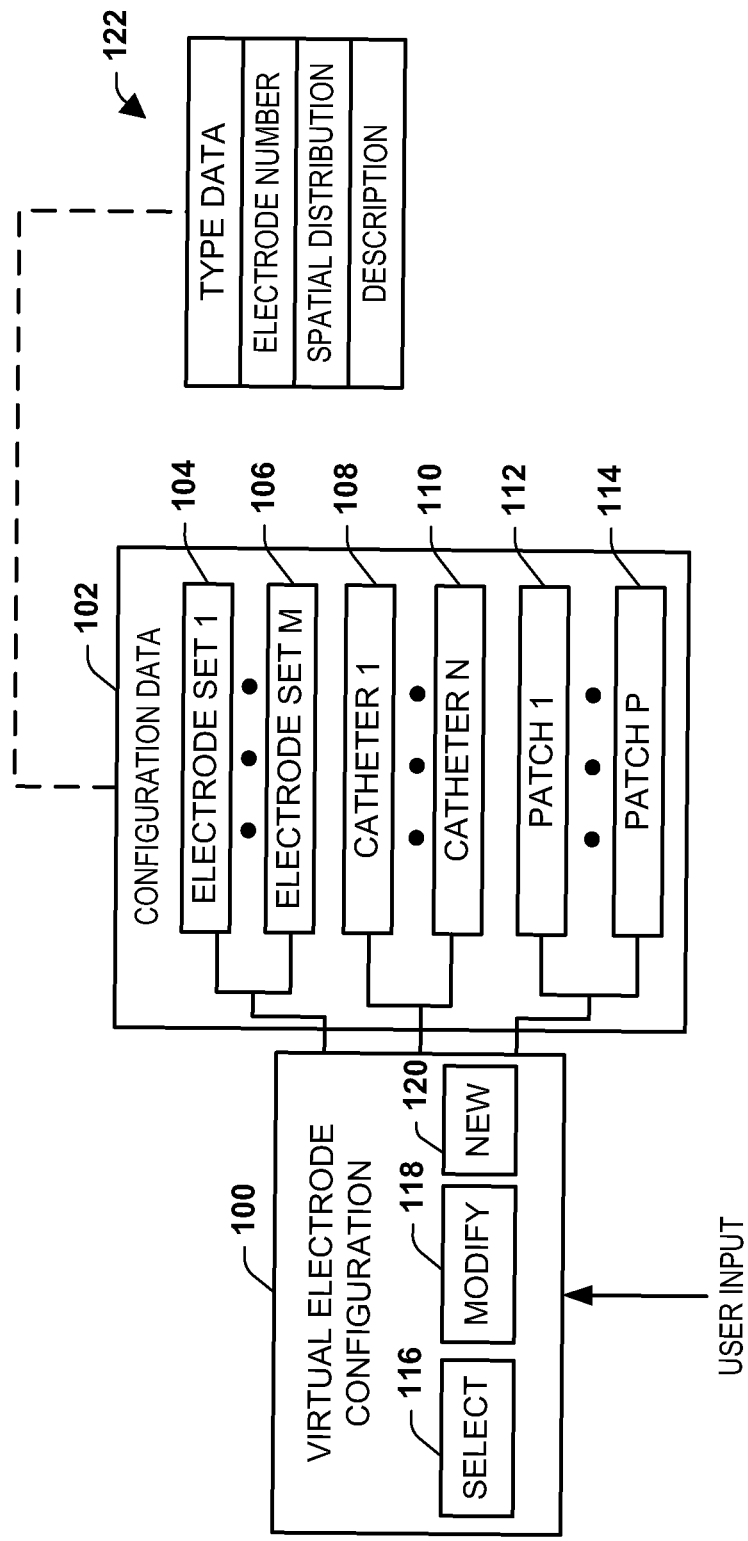
FIG. 5 depicts an example block diagram of user interface controls that can be utilized for configuring a virtual electrode from a predefined arrangement of electrodes in accordance with an aspect of the invention.

FIG. 5 depicts an example of an electrode configuration module 100 that can be employed by a user for selecting from among a plurality of predefined different electrode configurations. Configuration data 102 is associated with the electrode configuration element 100 and includes data 122 that parameterizes a plurality of different virtual electrode configurations.

As depicted in FIG. 5 the configuration data 102 can include one or more sets of electrodes 104 and 106, indicated at ELECTRODE SET 1 and ELECTRODE SET M, where M is an integer denoting a number of different sets of electrode configurations in the configuration data 102. Each of the electrodes 104-106 can include an arrangement of one-dimensional, two-dimensional or three-dimensional electrodes having a particular spatial distribution and electrical properties associated therewith, which can be represented as a mathematical model for each configuration.

The configuration data 102 can also be programmed to parameterize a plurality of electrophysiology catheters 108 and 110, indicated at CATHETER 1 through CATHETER N, where N is an integer denoting the number of different catheters to chose from in the configuration data. Each of the catheters 108-110 includes a set of parameters that defines the spatial distribution of one or more electrodes on each respective catheter 108 and 110 as well as other parameters (e.g., electrical parameters such as capacitance, resistivity or the like) that may affect measurements that would be made by the catheters.

The configuration data 102 can also include one or more patches 112 and 114, indicated at PATCH 1 through PATCH P, where P is an integer denoting the number of available predefined patch configurations in the configuration data 102. Each patch 112-114 can have a different predefined configuration of electrodes distributed across a two-dimensional surface. The surface can be planar or it can be curved. Alternatively, the patch surface can be conformable such that it varies according to the surface geometry of the surface region where the patch is positioned. Thus, each electrode in a conformable patch will, when positioned on a representation of a patient model, conform its position to the adjacent surface, thereby allowing tortuous curved anatomical surfaces to be evaluated.

Catheters 108-110, electrodes 104-106 or patches 112-114 may include configurations of commercially available devices. A user can employ the system 10 (FIG. 1) to generate a representation of physiological data commensurate with that which can be generated by physically placing a selected commercially available product (e.g., patch or electrophysiology catheter) in or near a patient's organ, but can now obtain such information in a non-invasive manner without actually placing such electrodes, or catheters or patches within the patient's body. That is, as described herein, systems and methods implementing the invention can employ electrophysiology data from any source and provide a representation that is consistent with data that may be derived from any type of electrode configuration (or configurations), which can be defined by the user or otherwise generated by the system.

As an example, a user can employ the electrode configuration module 100 to select from one of the plurality of predefined electrode configurations 104-114. The user can also modify the selected electrode configuration as desired to provide a user-defined or modified version thereof. For instance, a user can select the MODIFY interface element 118 and be provided a dialog box or other user-entry element that can be used to change parameters, such as the number of electrodes and/or the spatial distribution of electrodes for a given selected electrode configuration. Additionally, the configuration component 100 can include a new user interface element 120 that can be employed to define and generate a new user-defined electrode configuration. The new configuration can be defined in terms of its geometry, electrical and other properties.

Configuration data for each virtual electrode structure available to the user can employ a data structure 122 for storing parameters and metadata associated with the electrode configuration. For example, as depicted in FIG. 5, the data structure 122 can include type data, number of electrodes, a spatial distribution of the electrodes as well as a textual description. The textual description can be editable by the user as is known in the art.

Figure 6:
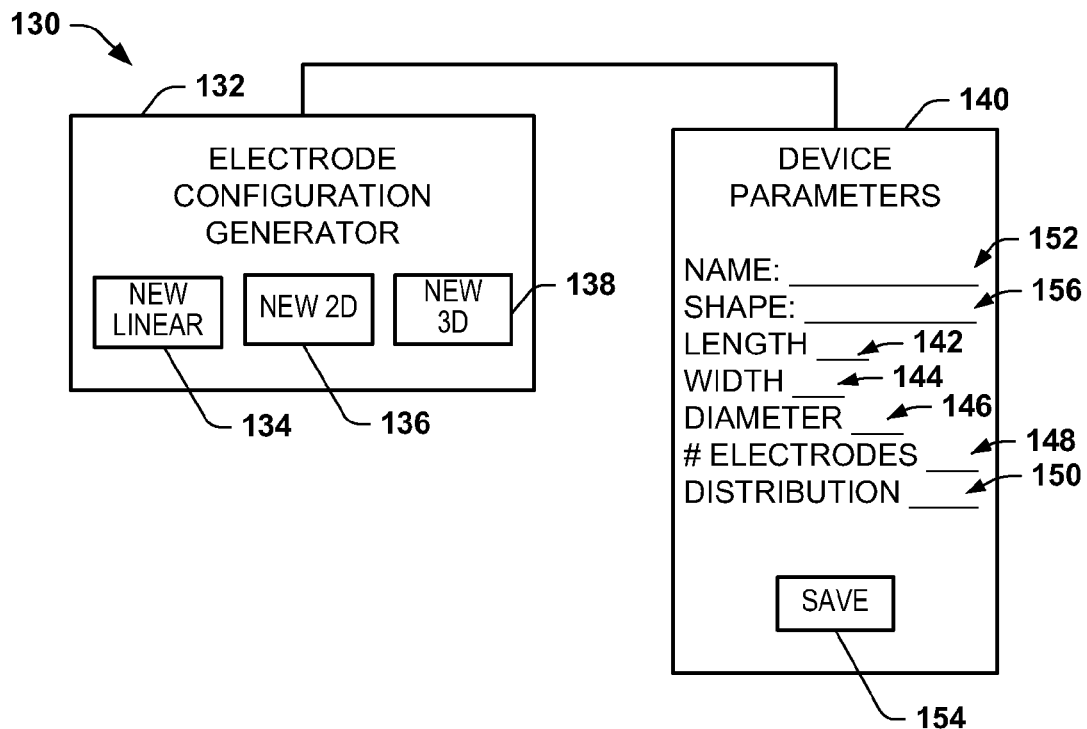
FIG. 6 depicts an example block diagram of user interface controls that can be utilized for configuring a virtual electrode in accordance with an aspect of the invention.

As a further example, FIG. 6 depicts an example of a functional block diagram of a system 130 that can be employed to configure one or more user-defined electrode. The system 130 includes an electrode configuration generator component 132 that includes or otherwise employs functions and methods programmed to facilitate construction of a virtual electrode structure having user-defined characteristics and parameters. The electrode configuration generator 132 can provide user interface elements 134, 136 and 138, such as in the form of graphical buttons, tabs or the like, which can access functions for parameterizing different types of custom configurations. The user interface element 134 can access methods for generating a new linear type of electrode configuration. The user interface element 136 can access methods for defining a new two-dimensional electrode configuration (e.g., a patch). The user interface element 138 can be utilized for constructing a new three-dimensional electrode configuration. In response to selecting any of such user interface elements 134, 136 or 138, an appropriate dialog or other user interface mechanism, schematically indicated at 140, can be provided to the user for entering configuration information.

In the example of FIG. 6, the dialog 140 can be provided to the user to selectively enter respective parameters appropriate to the type of electrode configuration selected by the user. That is, the dialog 140 and the information requested from the user can vary depending on the type of electrode configuration. For instance, a user can define the length of the electrode structure, indicated at 142, a width of the structure, indicated at 144, and a diameter of the device, indicated at 146. The device parameters dialog 140 can also allow the user to identify and define the number of electrodes, indicated at user entry 148, as well as the spatial distribution of the electrodes, indicated at 150.

As a further example, the spatial distribution 150 of electrodes further may be fixed by defining a distance between electrodes, which distance may be uniform or variable along the device. Alternatively or additionally, the geometry and placement of electrodes can be defined based on anatomical features of the representation of the heart (patient specific or a general model), such as by arranging electrode according to selected anatomical landmarks. In addition to or as another alternative, the arrangement and distribution of electrodes can be determined dynamically based on electrical data for the patient.

The user can also input a name for the electrode configuration in a name entry element 152. If the user does not enter such a name, a name can automatically be generated for each electrode configuration that the user defines. Upon setting the set of parameters, a user can save the device by activating a "save" user interface element 154. Once a configuration has been created, such configuration can be available subsequently for selection as a predefined electrode configuration, such as described herein.

The device parameters 140 can also include a shape parameter 156, which can be utilized to define a shape of the virtual structure, such as a loop, a spiral, a rectangle or annular shape. Those skilled in the art will understand and appreciate various other types of information and different mechanism that can be employed by a user to enter similar types of user-defined configuration data, including both graphical and textual methods.

Figure 7:
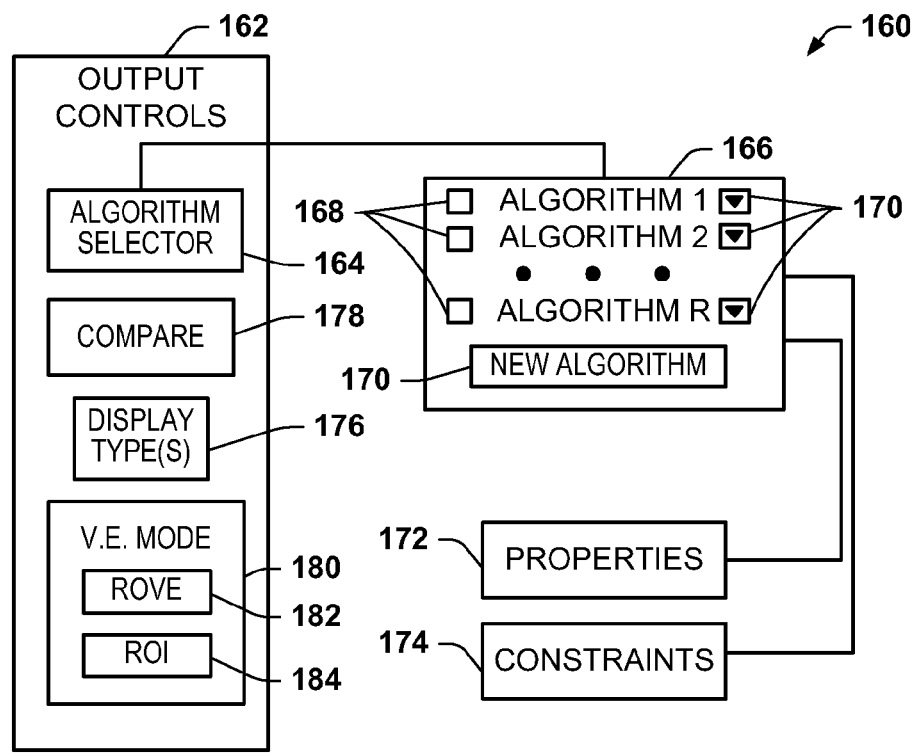
FIG. 7 depicts an example of a block diagram of controls and associated methods that can be utilized for configuring virtual electrodes in accordance with an aspect of the invention.

FIG. 7 depicts an example of an output control module 160 that can be utilized to control the type of information provided in a virtual electrode output representation as well as the form and content in the representation. The output control 160 can include an algorithm selector 162 that is programmed to provide a user interface element, schematically indicated at 164, that enables a user to select one or more algorithms that are used to perform computations for use in populating an output representation generated in accordance with an aspect of the invention.

In the example of FIG. 7, the algorithm user interface element 164 is depicted as including a plurality of predefined algorithms that a user can select and program to generate corresponding physiological data that can be visually represented to the user. For instance, the algorithm user interface element 164 includes a list of algorithms 166, indicated at ALGORITHM 1, 2 through ALGORITHM R, where R is a positive integer denoting the number of algorithms. Each of the algorithms 166 can be programmed to compute corresponding physiological data for an assigned virtual electrode (based on electrode configuration data) that has been positioned relative to a representation of the patient's organ (based on position data) such as described herein. Furthermore, the user can dynamically assign one or more algorithms, including digital signal processing algorithms or other computations, for each virtual electrode. The results set for each computation or signal processing can be employed to generate a corresponding representation for each virtual electrode. Alternatively or additionally, a general computation, such as statistical and/or comparative analysis, can be performed on all or a selected portion of the virtual electrodes.

In the example of FIG. 7, a user can select a respective algorithm to be active, such as by turning "ON" the algorithm by checking an appropriate check box, indicated at 168 for each algorithm. Those skilled in the art will understand and appreciate that various other user interface elements (e.g., context menus or buttons) can be utilized to selectively control the algorithms. Each of the algorithms can include a user interface element, indicated at 170, such as a graphical feature for activating a drop down context menu or dialog. For instance, in response to activating the user interface element 170 for a given algorithm, a user can access to a corresponding programming dialog, which the user can employ to define properties 172 associated with the selected algorithm. The properties 172 can include setting one or more time intervals, or selecting one or more data set that the associated algorithm will utilize for generating a corresponding set of results. A user-entry dialog, indicated at 174, can also be provided through which the user can enter associated constraints associated with the selected algorithm. The constraints entry dialog 174 for a given algorithm can include a mechanism to select a subset of the electrodes as well as to define input or output limits or other parameters associated with the algorithm.

Each of the algorithms can define a type of information to be provided in the resulting output representation. The algorithms can range in complexity from providing types of data that can be measured or computed easily by an actual electrode (e.g., electrical potential, activation time) to providing more complex statistical and comparative types of information. One type of data can be considered a look-up or measured value, such as including electric potential activation time, frequency of the electrophysiological signals for the selected electrode configuration. Other types of data can provide information that can be computed based upon such measured variables, such as including a gradient of any variable or the statistics of variables, such as including a mean, maximum or minimum. It is to be appreciated that any such variables or statistics thereof can be computed spatially with respect to the organ and the virtual electrode configuration that is positioned relative to the organ as well as temporally over a time period or selected interval thereof during which the electrophysiology data has been acquired. The temporal range can be defined as part of the constraints 174 or properties 172 for a given selected algorithm.

In a situation where multiple electrode configurations or electrophysiology catheters have been virtually positioned at selected anatomical positions, a set of one or more algorithms can be assigned to each respective virtual electrode for displaying corresponding data to the user as part of the output representation. Thus, there can be multiple output representations and an arrangement of displays depending on the type of information that is being displayed can be controlled via the output control 160 and, in particular, by a display type element 176. The display type element 176 can be utilized to access graphics control methods that are programmed to control, for example, whether the output is in a text based form or a graphical form that is superimposed over the select organ and relative to a graphical representation of the selected electrode configuration and/or waveform representation.

In addition to affording the user an opportunity to select any number of one or more algorithms and apply such algorithms to any number of one or more virtual electrode configurations, the output control 150 includes a compare interface element 178 that can access methods and functions programmed to generate comparative data. The comparative data can be a spatial comparison (e.g., between different virtual electrodes or different anatomic positions), a temporal comparison (e.g., the same virtual electrodes at different instances in time), or a spatial-temporal comparison (e.g., different virtual electrodes at different time instances), which can vary depending on the type of data that is being compared. The compared data further can compare similar types of information derived for different virtual electrode configurations.

As an example of temporal comparative data, the compare interface element 178 can be utilized to compare one or more measured values for a same given anatomic location (e.g., corresponding to the same virtual electrode configuration) for different cardiac intervals. For instance, a user can employ the compare user interface element 166 to provide a comparison of earliest activation time for a first interval relative to the earliest activation time for a second user-defined interval, which results can be displayed on an output representation either superimposed on the same representation or as a side-by-side comparison on two separate representations. Corresponding isochrone maps can be provided for each of the intervals being compared to provide further comparative information.

As yet a further example, bipolar data can be constructed from unipolar electrograms data, such as by subtracting electrophysiology data that had been determined between two different virtual electrodes. The two different virtual electrodes can be chosen automatically, such as each pair being chosen by applying a nearest neighbor algorithm. Alternatively, the electrode pairs can be user definable, such as by using a pointer and selecting the electrodes or by identifying the electrodes by name in a text based data entry method.

One or more algorithms can also be utilized to dynamically determine or identify one or more anatomical meeting user-defined criteria, such as according to a user-selected an algorithm or function range. As an example, a user may set activation time limits, and a virtual patch electrode configuration which satisfies the activation time limits can be dynamically constructed and displayed to the user as positions of interest.

As a further example, criteria can be set to find all dominant frequencies over the entire organ or a selected region of the organ. All points and locations meeting the defined criteria thus can be represented (e.g., graphically) to the user. For instance, the results can be employed to dynamically construct a graphical representation of a virtual electrode configuration that identifies which parts of the organ satisfy the criteria.

Alternatively or additionally, a user can employ the identified locations and select one or more virtual electrode configurations that can be placed at the identified locations for subsequent processing an application of one or more selected algorithms. Thus, it is to be appreciated that the output controls 162 can be programmed to locate regions of interest (based on user-defined criteria) that can be utilized for further evaluation in a non-invasive manner. Those skilled in the art will appreciate other criteria (e.g., a set of one or more algorithms or functions) can be utilized to dynamically construct a set of electrodes satisfying such criteria.

The output control 150 can also include a virtual electrode mode control element 180. The virtual electrode mode control 180 allows the user to select from one of a plurality of different virtual electrode modes, each of which can control how resulting physiological information is presented. For example, the virtual electrode mode 180 can include a rove or roving control 182 that can be activated to implement a roving mode. In the roving mode, the cursor or other graphical object, such as a graphical representation of a selected virtual electrode structure, can be moved relative to the graphical representation of the surface region (e.g., of the patient's heart) such that the system dynamically generates a graphical representation of the physiological data as a function of the current location of the cursor relative to the surface region. Thus, as the cursor or other graphical object is moved across the surface region, the output graphical representation is modified to reflect changes in electrical information for the current location. The output can also move commensurate with movement of the cursor or other graphical object.

Figure 8:
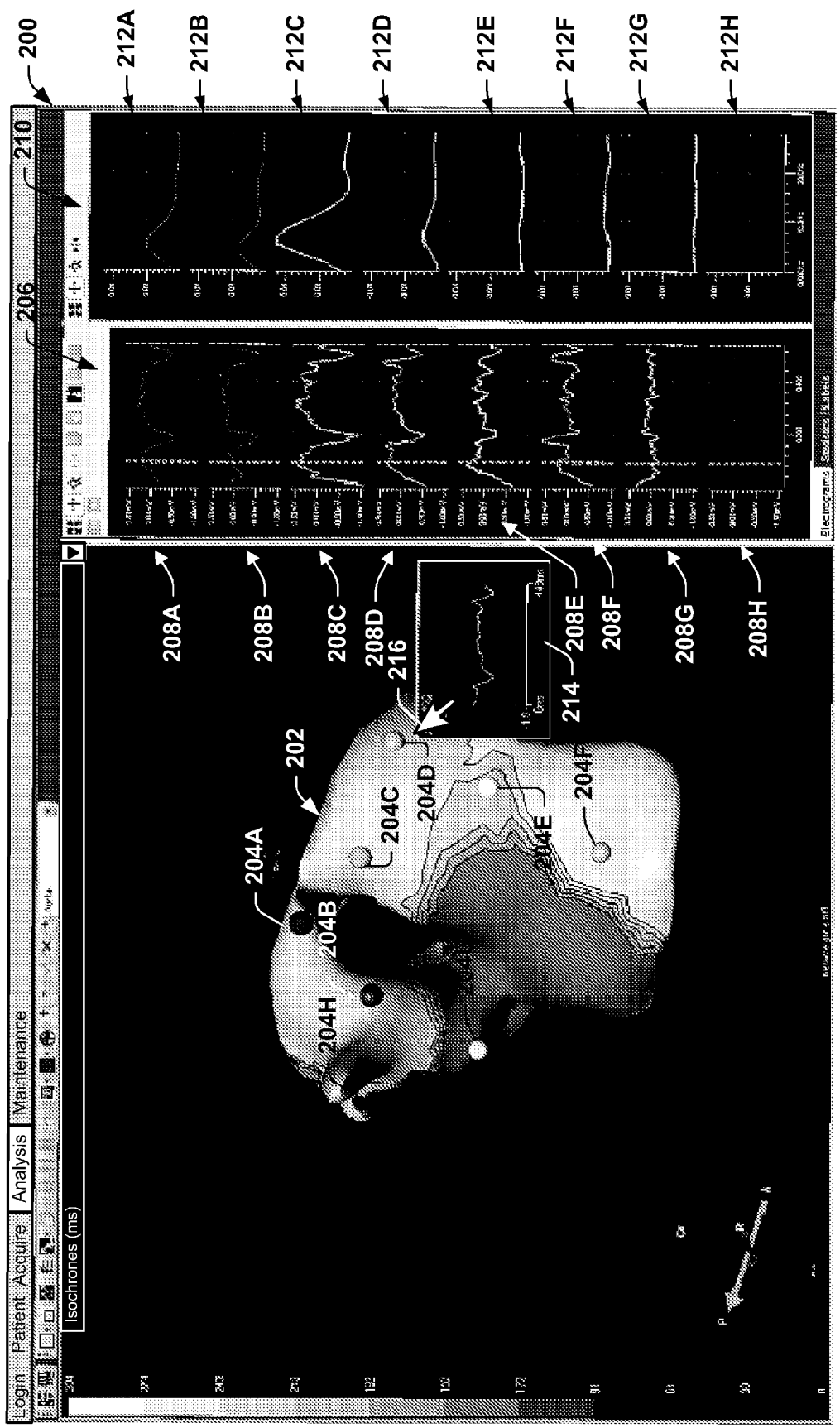
FIG. 8 depicts an example of a graphical user interface for a visualization system that implementing a roving virtual electrode in accordance with an aspect of the invention.

An example GUI 200 that demonstrates the roving mode relative to a three-dimensional surface model of a heart 202 is depicted in the example of FIG. 8. In FIG. 8, a plurality of virtual electrodes 204A, 204B, 204C, 204D, 204E, 204F, 204G and 204H have been placed at desired locations across the graphical electrical representation of the three-dimensional surface 202. For each (or at least a portion) of the virtual electrodes 204A, 204B, 204C, 204D, 204E, 204F, 204G and 204H positioned on the surface region 202 one or more corresponding output graphical representations are displayed. For example, a first window 206 can be utilized to display an electrogram 208A, 208B, 208C, 208D, 208E, 208F, 208G and 208H for each of the virtual electrodes 204A, 204B, 204C, 204D, 204E, 204F, 204G and 204H.

Adjacent to the electrogram window 206 in the example of FIG. 8 is a frequency window 210 that includes a power spectrums 212A, 2128, 212C, 212D, 212E, 212F, 212G and 212H (demonstrated in amplitude versus frequency) for each of the virtual electrodes 204A, 204B, 204C, 204D, 204E, 204F, 204G and 204H.

FIG. 8 also depicts an output graphical representation of physiological data (an electrogram), indicated at 214, which corresponds to electrical activity at a position defined by the position of the cursor 216. In this example, the electrogram 214 is partially superimposed on the surface region patient's heart 202. It would be appreciated that, if the cursor were to move across the surface of the heart 202, the physiological data being displayed in the window would vary according to the position. Additionally, the representation can move commensurate with the movement of the cursor 216, as to remain adjacent to the cursor during the roving mode. In this way a user can scan across the surface of the organ and rapidly ascertain variations in the electrogram or other electrophysiological data that can be displayed.

Referring back to FIG. 7, the virtual electrode mode 180 can also display a region of interest mode 184 in which a user can define a series of points or virtual electrodes in one region and then another set of points in another region. Methods can be employed to analyze and compare selected information relative to each other to provide additional information to the user.

Figure 9:
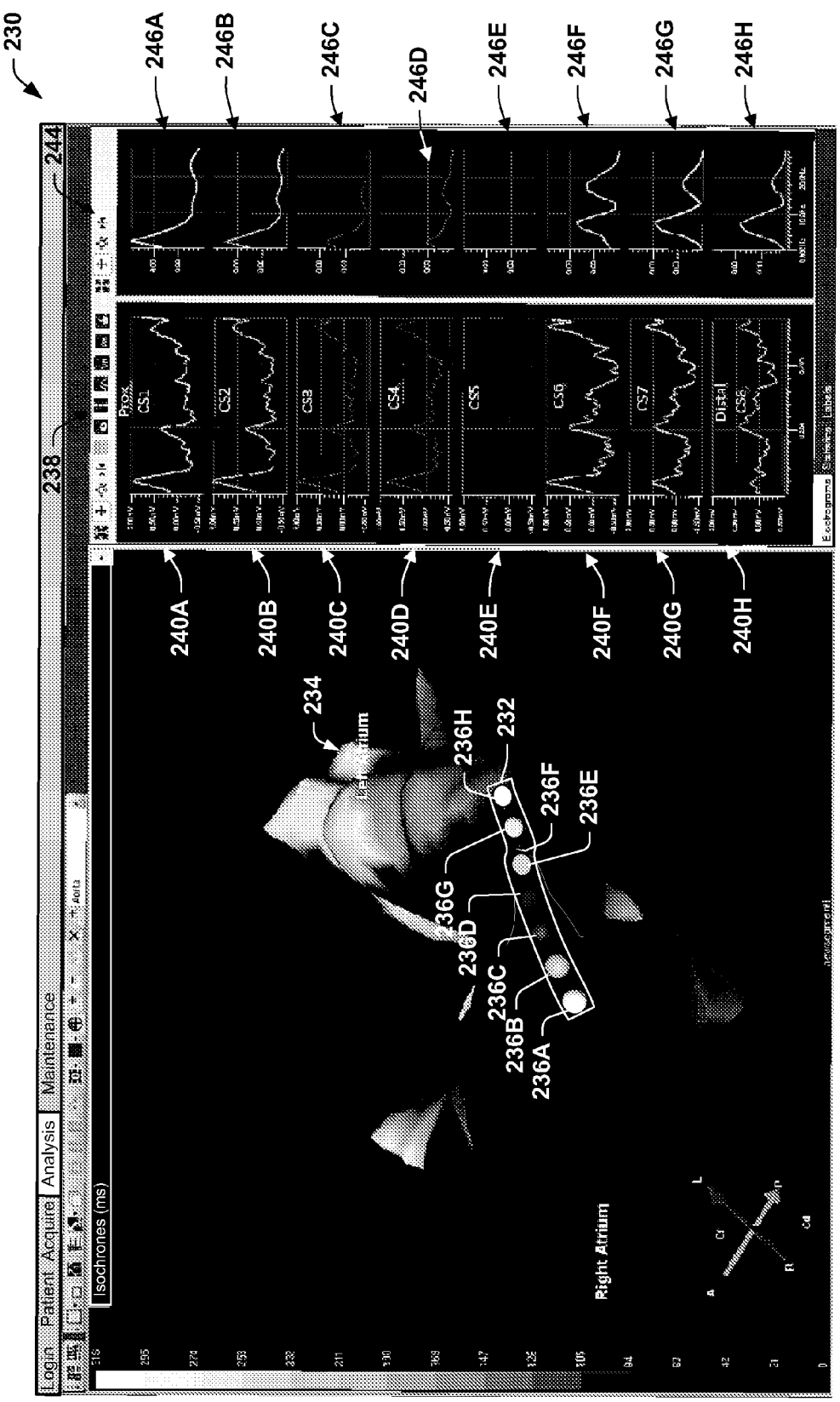
FIG. 9 depicts an example of a graphical user interface for a visualization system implementing a multi-pole virtual electrode on the coronary sinus in accordance with an aspect of the invention.

FIG. 9 depicts an example of another GUI 230 for another virtual electrode structure configured as a linear catheter 232 positioned on a patient's heart model 234. In the example of FIG. 9, the virtual catheter 232 includes a linear arrangement of virtual electrodes 236A, 236B, 236C, 236D, 236E, 236F, 236G and 236H distributed along its length. For example, the virtual electrode structure 232 can correspond to a linear catheter configuration that has been placed over coronary sinus (CS) 238 of the patient's heart 234. For the coronary sinus catheter configuration, one or more corresponding representation of physiological data can be provided for each respective electrode in the catheter structure. For example, a first window 238 can provide electrograms 240A, 240B, 240C, 240D, 240E, 240F, 240G and 240H generated based on location data for each of the respective virtual electrodes 236A, 236B, 236C, 236D, 236E, 236F, 236G and 236H on the structure 232. Similarly, a second window 244 can include power spectrum plots 246A, 246B, 246C, 246D, 246E, 246F, 246G and 246H generated for each of the electrodes 236A, 236B, 236C, 236D, 236E, 236F, 236G and 236H in the virtual structure 232.

The virtual electrodes 236A, 236B, 236C, 236D, 236E, 236F, 236G and 236H in the catheter structure 232 can conform to the surface of the heart 234 at which the virtual electrode structure is positioned. Thus in the example of FIG. 9, the virtual electrode corresponding to electrogram CS6 is partially obstructed as it is recessed at a corresponding recessed surface location in the coronary sinus.

Figure 10:
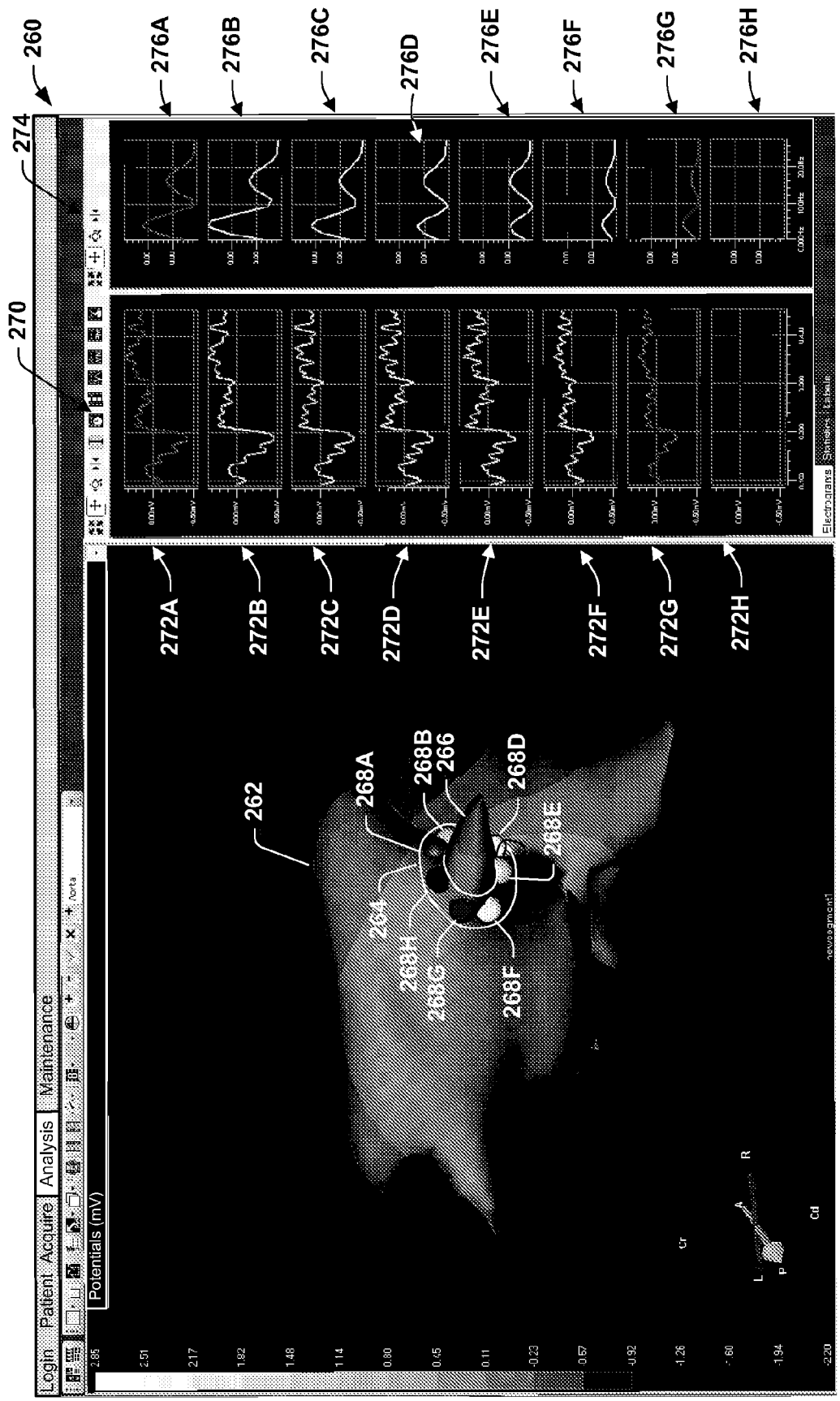
FIG. 10 depicts an example of a graphical user interface for a visualization system implementing another embodiment of a multi-pole ring virtual electrode around the pulmonary vein in accordance with an aspect of the invention.

FIG. 10 illustrates an example of another GUI 260 depicting a surface model representation 262 of a patient's heart for another type of catheter, indicated at 264. The catheter 264 is configured in an annular or ring configuration and is positioned in a circumscribing relationship around the pulmonary vein 266. For example, a virtual catheter of this type can be positioned around the pulmonary vein and measure potentials such as for lesion confirmation associated with an atrial fibrillation procedure, which may occur concurrently with the display in FIG. 10. Thus as described herein, the data set can be acquired previously or the data being utilized can be acquired in real time and converted to the corresponding electrode anatomical surface data for which the resulting display is shown and modified in real time accordingly.

The ring-shaped virtual catheter structure 264 includes an arrangement of virtual electrodes 268A, 268B, 268C, 268D, 268E, 268F, 268G and 268H distributed along the ring-shaped configuration. In the example of FIG. 10, one or more corresponding representation of physiological data can be provided for each respective electrode in the catheter structure. For example, a first window 270 can display electrograms 270A, 270B, 270C, 270D, 270E, 270F, 270G and 270H generated based on location data for each of the respective virtual electrodes 268A, 268B, 268C, 268D, 268E, 268F, 268G and 268H. Similarly, a second window 272 can include power spectrum plots 274A, 274B, 274C, 274D, 274E, 274F, 274G and 274H generated for each of the electrodes 268A, 268B, 268C, 268D, 268E, 268F, 268G and 268H.

Figure 11:
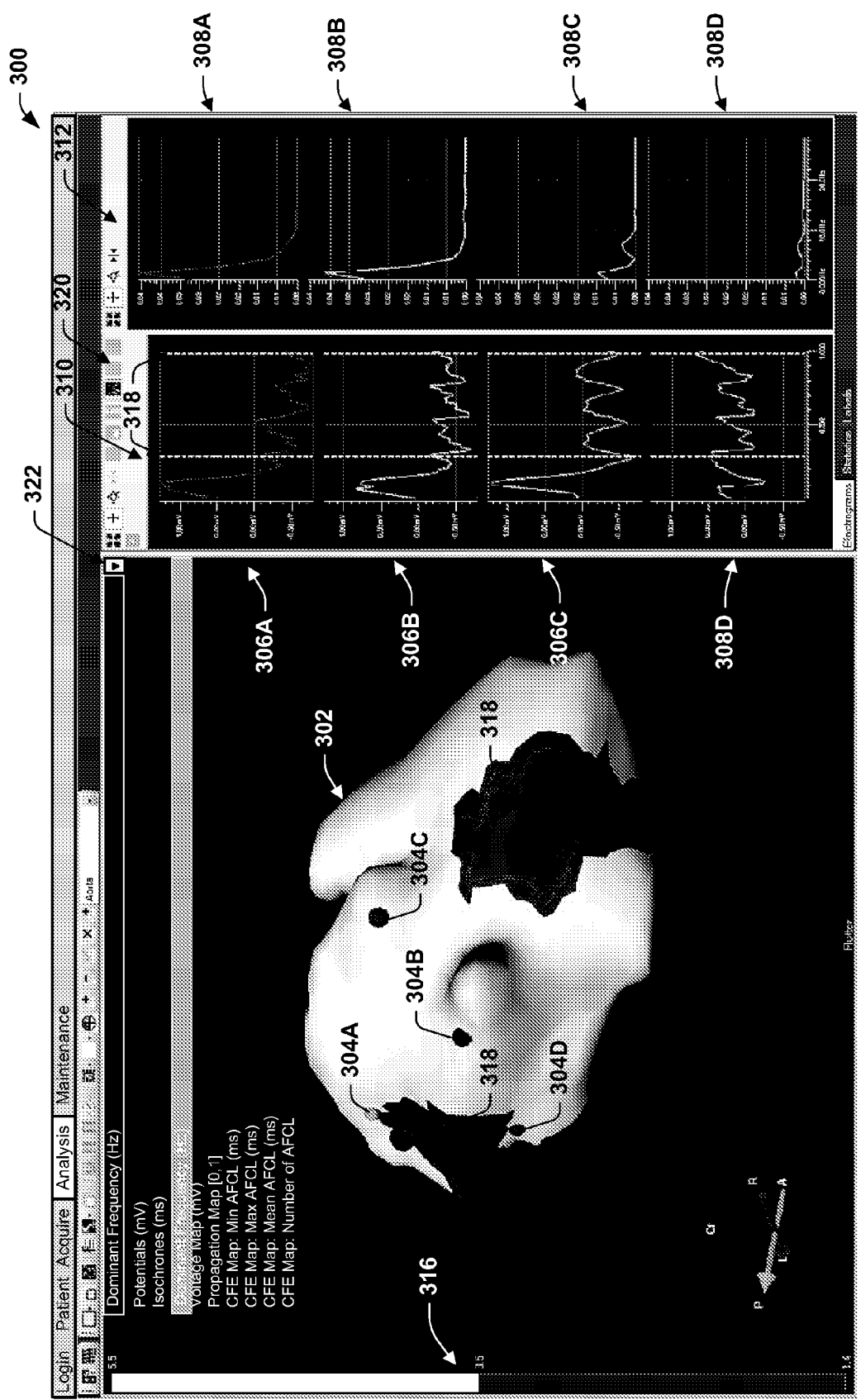
FIG. 11 depicts an example of a graphical user interface for a visualization system illustrating frequency information that can be implemented in accordance with an aspect of the invention.

FIG. 11 depicts an example GUI 300 in which mapping controls have been activated to depict a dominant frequency map superimposed on the graphical representation of the patient's heart, indicated at 302. In the example of FIG. 11, four virtual electrodes 304A, 304B, 304C and 304D are positioned at desired locations on a patient's heart. Corresponding electrograms 306A, 306B, 306C and 306D and power spectrum plots 308A, 308B, 308C and 308D are depicted in respective windows 310 and 312.

Additionally in FIG. 11, the dominant frequency map provides spatial information about the dominant frequency over the surface of the heart 302 according to a corresponding to a scale 314, such as can be implemented as a color code or gray scale code. Thus, reference to the scale 314 when viewing the dominant frequency map of the heart 302 demonstrates to the user the dominant frequency for each region of the heart. The dominant frequency can vary according to the interval for which the dominant frequency is computed. Thus in FIG. 11, caliper user interface elements 318 can be provided in the electrogram window, for example, to enable a user via a pointer or cursor to select or vary a time interval for which the dominant frequency is calculated. The caliper user interface element 318 can be activated for selecting the interval in response to activating a corresponding interval selector element 320, such as a button or other user interface feature.

Also depicted in FIG. 11 is a user interface element (e.g., a drop down context menu) 322 that defines what type of electroanatomic map is superimposed on the heart 302. Thus, in the example of FIG. 11, dominant frequency is selected, resulting in the map shown. It will be appreciated that other types of maps could be selected by a user (via the user interface element 322) for display superimposed on the heart, such as shown and described herein.

Figure 12:
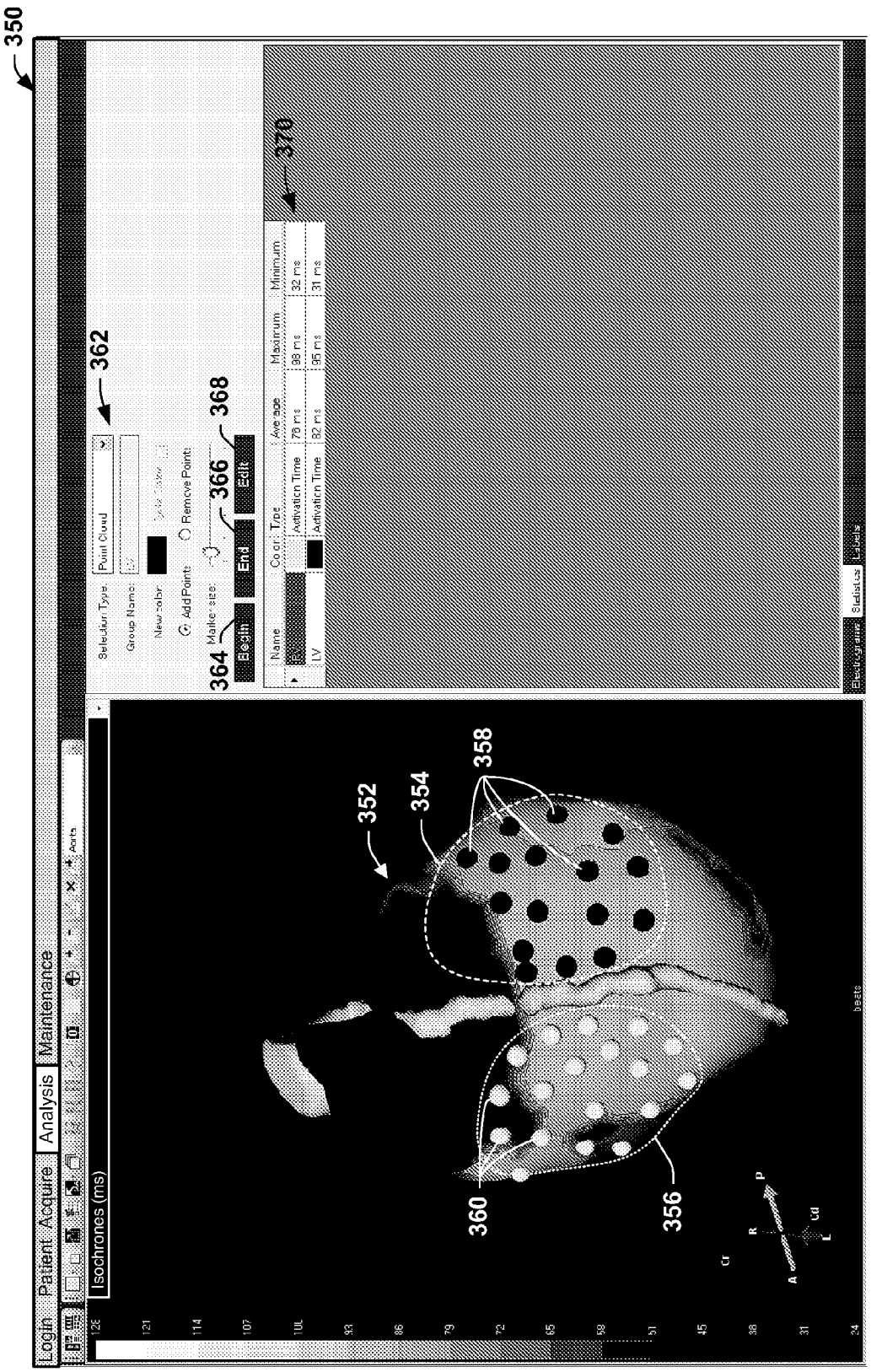
FIG. 12 depicts an example of a graphical user interface for a visualization system illustrating region of interest analysis that can be implemented in accordance with an aspect of the invention.

FIG. 12 depicts an example GUI 350 in which region of interest analysis has been activated for evaluation of electrophysiology of one or more regions on a surface of a patient's heart 352. In the example of FIG. 12 two regions have been identified for evaluation, indicated by dashed lines 354 and 356. Those skilled in the art will appreciate various methods that can be utilized to select the regions. As one example, a user can position individual virtual electrodes on each region of interest 354 and 356, such as placing electrodes 358 in region 354 and virtual electrodes 360 in region 356. In the illustrated example, the region 354 corresponds to the patient's left ventricle and the region 356 corresponds to the patient's right ventricle.

GUI controls 362 can be provided in an adjacent window, such as to control the color, size and method utilized to mark each region of interest with the virtual electrodes. The GUI controls 362 can also be utilized to selectively remove or edit placement virtual electrodes or portions of each region.

By way of example, a selection mode can be entered for a given region by selecting a begin user interface element (e.g., a button) 364. After placing a desired number of virtual electrodes on the region, a user end the placement mode for that region via another user interface element 366. Another user interface element 368 can be utilized for editing the number or distribution of virtual electrodes for a given region.

Other approaches can be employed to mark a region for analysis. For instance, a user can employ a drawing tool or similar user interface feature to identify each one or more region 354 and 356 on the heart 352. Each identified region can then be automatically populated with an arrangement of virtual electrodes 358 and 360. The number and spatial distribution of electrodes can be programmed by the user. As yet another alternative approach, a list of predefined anatomical landmarks (based on patient geometry data) can be provided to the user for selection. Each selected landmark can be automatically populated with a set of one or more virtual electrodes for analysis.

Once a region 354, 356 has been configured as a virtual electrode structure, electrical information can be displayed in an adjacent display window 370. Information associated with the electrical activity of each region can be provided according to the configuration and placement of virtual electrodes. The information can include statistical information for each region, such as the average, maximum and minimum activation time. A corresponding electroanatomical map can also be superimposed on the surface of the heart 352 (e.g., an isochrone map depicted in the example of FIG. 12). Those skilled in the art will understand and appreciate various other types of information that can be computed and presented to the user based on the arrangement of virtual electrodes 358 and 360, which can include numerical values as well as graphical information.

Figure 13:
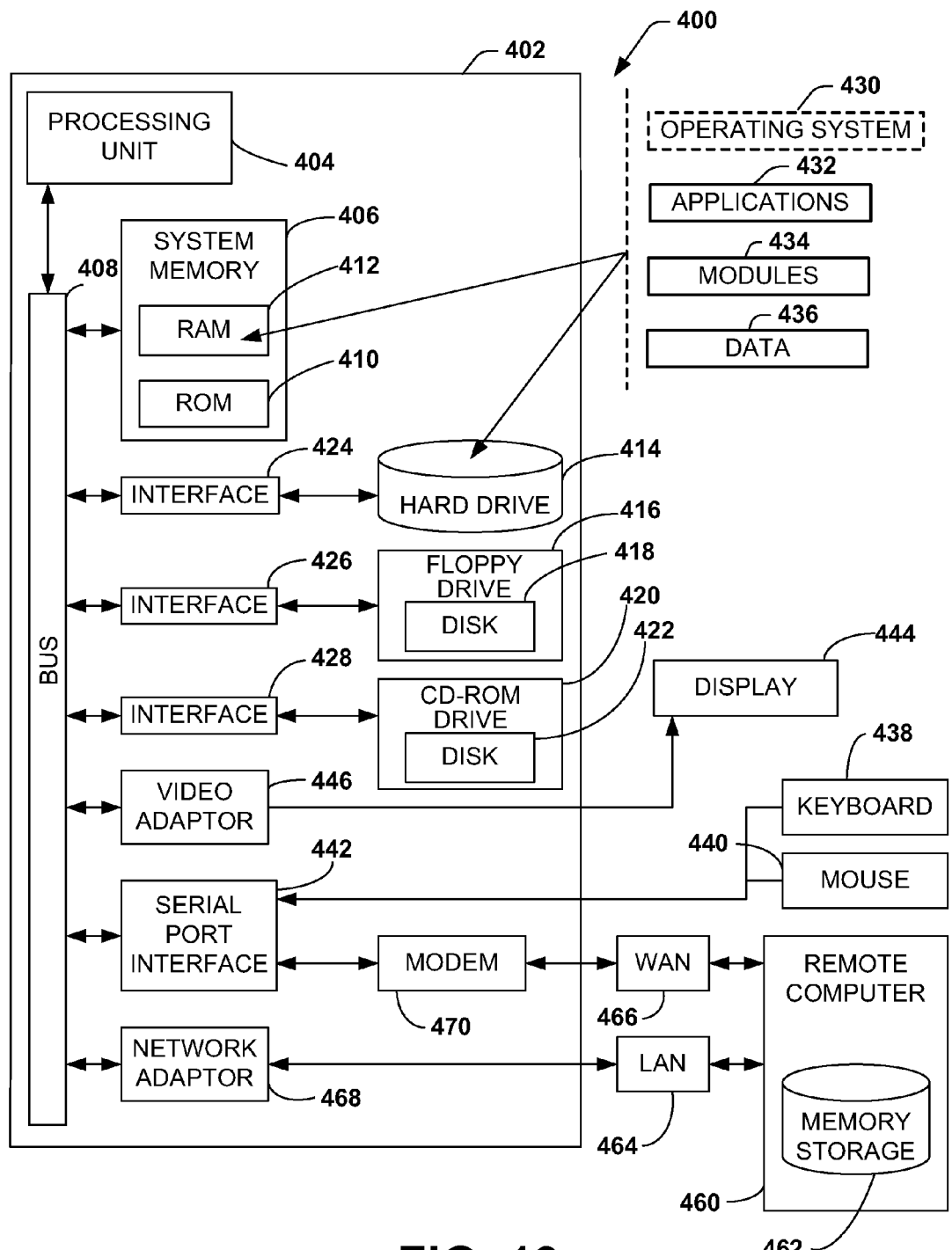
FIG. 13 depicts an example of a computer operating environment that can implement systems and methods according to an aspect of the invention.

FIG. 13 depicts an example of computer system 400 of the type that can be utilized to implement one or more embodiments of the systems and methods described herein for visualizing physiological data relating to a patient's organ. The computer system 400 can be implemented on one or more general purpose networked computer systems, embedded computer systems, routers, switches, server devices, client devices, various intermediate devices/nodes and/or stand alone computer systems. Additionally, the computer system 400 or portions thereof can be implemented on various mobile or portable clients such as, for example, a laptop or notebook computer, a personal digital assistant (PDA), and the like.

The system bus 408 may be any of several types of bus structure including a memory bus or memory controller, a peripheral bus, and a local bus using any of a variety of conventional bus architectures such as PCI, VESA, Microchannel, ISA, and EISA, to name a few. The system memory 406 includes read only memory (ROM) 410 and random access memory (RAM) 412. A basic input/output system (BIOS), containing the basic routines that help to transfer information between elements within the computer 402, such as during start-up, is stored in ROM 410.

The computer 402 also may include, for example, a hard disk drive 414, a magnetic disk drive 416, e.g., to read from or write to a removable disk 418, and an optical disk drive 420, e.g., for reading from or writing to a CD-ROM disk 422 or other optical media. The hard disk drive 414, magnetic disk drive 416, and optical disk drive 420 are connected to the system bus 408 by a hard disk drive interface 424, a magnetic disk drive interface 426, and an optical disk drive interface 428, respectively. The drives and their associated computer-readable media provide nonvolatile storage of data, data structures, computer-executable instructions, etc. for the computer 402. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, may also be used in the exemplary operating environment 400, and further that any such media may contain computer-executable instructions for performing the methods of the present invention.

A number of program modules may be stored in the drives and RAM 412, including an operating system 430, one or more application programs 432, other program modules 434, and program data 436. The operating system 430 in the computer 402 could be any suitable operating system or combinations of operating systems. The application programs 416, other program modules 417, and program data 418 can cooperate to provide a visualization of output results for a patient's organ, such as shown and described herein.

A user may enter commands and information into the computer 402 through one or more user input devices, such as a keyboard 438 and a pointing device (e.g., a mouse 440). Other input devices (not shown) may include a microphone, a joystick, a game pad, a satellite dish, a scanner, or the like. These and other input devices are often connected to the processing unit 404 through a serial port interface 442 that is coupled to the system bus 408, but may be connected by other interfaces, such as a parallel port, a game port or a universal serial bus (USB). A monitor 444 or other type of display device is also connected to the system bus 408 via an interface, such as a video adapter 446. In addition to the monitor 444, the computer 402 may include other peripheral output devices (not shown), such as speakers, printers, etc. Thus, the output representation for a virtual electrode is not limited to a graphical representation on a display.

The computer 402 may operate in a networked environment using logical connections to one or more remote computers 460. The remote computer 460 may be a workstation, a server computer, a router, a peer device, or other common network node, and typically includes many or all of the elements described relative to the computer 402, although, for purposes of brevity, only a memory storage device 462 is illustrated in FIG. 15. The logical connections depicted in FIG. 15 may include a local area network (LAN) 464 and a wide area network (WAN) 466. Such networking environments are commonplace in offices, enterprise-wide computer networks, intranets, and the Internet.

When used in a LAN networking environment, the computer 402 is connected to the local network 464 through a network interface or adapter 468. When used in a WAN networking environment, the computer 402 typically includes a modem 470, or is connected to a communications server on an associated LAN, or has other means for establishing communications over the WAN 466, such as the Internet. The modem 470, which may be internal or external, is connected to the system bus 408 via the serial port interface 442. In a networked environment, program modules depicted relative to the computer 402, or portions thereof, may be stored in the remote memory storage device 462. It will be appreciated that the network connections shown are exemplary and other means of establishing a communications link between the computers 402 and 460 may be used.

In accordance with the practices of persons skilled in the art of computer programming, the present invention has been described with reference to acts and symbolic representations of operations that are performed by a computer, such as the computer 402 or remote computer 460, unless otherwise indicated. Such acts and operations are sometimes referred to as being computer-executed. It will be appreciated that the acts and symbolically represented operations include the manipulation by the processing unit 404 of electrical signals representing data bits which causes a resulting transformation or reduction of the electrical signal representation, and the maintenance of data bits at memory locations in the memory system (including the system memory 406, hard drive 414, floppy disks 418, CD-ROM 422, and shared storage system 410) to thereby reconfigure or otherwise alter the computer system's operation, as well as other processing of signals. The memory locations where such data bits are maintained are physical locations that have particular electrical, magnetic, or optical properties corresponding to the data bits.

Those skilled in the art will understand and appreciated various modifications and implementations of virtual electrodes that can be utilized. For example, an arrangement of one or more virtual electrodes may be transient or persistent. A transient or persistent virtual electrode structure can be created by a mouse click and drag operation, depending on the GUI mode. Thus, the transient virtual electrode or algorithms being applied can be modified and corresponding outputs being provided to the user via the GUI, while the parameters and output for the persistent arrangement remain fixed.

Furthermore, a virtual electrode structure may be hierarchically aggregated from a plurality of component virtual catheters, each performing its own computations, with the aggregate virtual catheter aggregating and further manipulating the results of its constituents. That is, each general algorithm being applied can correspond to a parent algorithm that is functionally defined as an aggregate of child algorithms. Each child algorithm can be computed for each respective electrode according to electrophysiology data and its anatomical position.

As an example, a dyssynchrony virtual electrode arrangement may correspond to a parent algorithm programmed to compare mean activation times from two separate virtual surface patches (as described above) placed on the left ventricle (LC) and right ventricle (RV) (e.g. free walls), and display on the GUI a difference between the mean activation times. Each of the virtual surface patches LV and RV can include child algorithms for each of the respective electrodes $LV\_1, LV\_2 \ldots LV\_P$ (where P is the number of electrodes on the LV patch) and $RV\_1, RV\_2 \ldots RV\_Q$ (where Q is the number of electrodes on the RV patch). The results of mean activation times computed for each of $LV\_1, LV\_2 \ldots LV\_P$ can be compared to $RV\_1, RV\_2 \ldots RV\_Q$ with the results of the comparison provided as a graphical representation superimposed on the patient's heart.

In view of the foregoing, those skilled in the art will appreciate the versatility and power of the systems and methods described herein. For example, methods can be programmed to dynamically create a virtual electrode structure based on inverse look-up based on any electrophysiological property or combinations thereof. The configuration and properties of such dynamically created electrode structures can be ascertained according to a set of parameters that satisfy particular constraints or extrema conditions. The constraints and conditions may be set, for instance, depending on patient electrophysiological information for a particular time or time interval of interest. The analysis can be performed in the time domain or in the frequency domain, for example, depending on the constraints and conditions being employed.

Systems and methods described herein can also utilize algorithms that can be fixed or they can be created dynamically. For example, the system can include programmed functionality that employs in-place editing and a scripting interface to mathematical libraries (e.g., similar to matlab or python) embedded in the system.

Those skilled in the art will further understand that the systems and methods described herein can be programmed to display temporal or frequency content or a histogram of any electrophysiological quantity. For example, corresponding user interface elements can be programmed to access functions and methods so that a user can select a set of one or more electrodes, in response to which various display can be generated corresponding to graphical and/or textual representations of corresponding electrophysiological parameters, such as including in a waveform view, a power spectra view, or histogram view to name a few.

What have been described above are examples and embodiments of the invention. It is, of course, not possible to describe every conceivable combination of components or methodologies for purposes of describing the invention, but one of ordinary skill in the art will recognize that many further combinations and permutations of the invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A computer-implemented method for visualizing physiological data of a patient, the method comprising:
    storing in memory electroanatomic data representing electrical activity for a predetermined surface region of the patient;
    providing an interactive graphical representation of the predetermined surface region of the patient;
    receiving a user input that defines location data corresponding to a user-selected location for at least one roving virtual electrode on the graphical representation of the predetermined surface region of the patient; and
    dynamically generating a graphical representation of the physiological data corresponding to a current location of the roving virtual electrode relative to the graphical representation of the predetermined surface region of the patient, such that the graphical representation of the physiological data is modified continuously responsive to changes in the current location of the roving virtual electrode as the roving virtual electrode is moved.

2. The method of claim 1, further comprising superimposing a graphical representation of the at least one roving virtual electrode on the interactive graphical representation of the predetermined surface region of the patient in response to the receiving of the user input.

3. The method of claim 1, wherein the graphical representation of the physiological data corresponding to the current location of the user interface pointing element is generated adjacent to the current location of the user interface pointing element.

4. A computer-implemented method for visualizing physiological data of a patient, the method comprising:
    storing in memory electroanatomic data representing electrical activity for a predetermined surface region of the patient;
    providing an interactive graphical representation of the predetermined surface region of the patient;
    receiving a user input that defines location data corresponding to a user-selected location for at least one virtual electrode on the graphical representation of the predetermined surface region of the patient; and
    dynamically generating a graphical representation of the physiological data corresponding to a current location of a user interface pointing element relative to the predetermined surface region of the patient, such that the graphical representation is modified automatically responsive to changes in the current location of the user interface pointing element;
    in response to receiving a corresponding user input, the graphical representation of the physiological data corresponding to user selected location location being maintained as a first graphical representation for a fixed virtual electrode at the user selected current location regardless of movement of the user interface pointing element; and
    dynamically generating a second graphical representation of the physiological data corresponding to a roving virtual electrode that is modified continuously responsive to changes in the current location of the roving virtual electrode as the roving virtual electrode is moved.

5. The method of claim 1, further comprising:
    assigning a configuration of the at least one virtual electrode; and
    storing the assigned configuration as electrode configuration data for the at least one virtual electrode, such that the visual representation of physiological data for the predetermined surface region is generated based on the location data, the electroanatomic data and the electrode configuration data.

6. The method of claim 5, wherein the electrode configuration data for the at least one virtual electrode further comprises a type of electrode configuration and a resolution that defines a number of one or more electrodes and a spatial relationship of the one or more electrodes.

7. The method of claim 6, further comprising:
    storing electrode template data that represents a plurality of predefined electrode templates corresponding to different electrode configurations; and
    setting the configuration data as corresponding to one of the plurality of different predefined electrode types in response to a user input selecting a respective one of the plurality of predefined electrode templates.

8. The method of claim 5, further comprising generating a graphical representation of the at least one virtual electrode based on the configuration data, the graphical representation of the at least one virtual electrode being independently moveable relative to the interactive graphical representation of the predetermined surface region of the patient.

9. The method of claim 7, wherein at least one of the plurality of predefined electrode templates further comprises different types of electrophysiology catheters.

10. The method of claim 7, wherein at least one of the plurality of predefined electrode templates further comprises a multi-dimensional arrangement of electrodes, the multi-dimensional surface conforming to a contour of the predetermined surface region of the patient at the user-selected location where the arrangement of electrodes is positioned such that each of the electrodes has a respective location corresponding to a location on the predetermined surface region of the patient.

11. The method of claim 1, wherein the electroanatomic data further comprises electroanatomic data computed for a plurality of points distributed across the predetermined surface region of the patient based on electrical data acquired from the patient.

12. The method of claim 11, further comprising selecting at least one time interval for the electroanatomical data in response to a user input, such that the visual representation of physiological data for the predetermined surface region of the patient comprises a graphical representation of patient electrical activity that is generated based on the location data and the electroanatomical data for the selected at least one time interval.

13. The method of claim 12, further comprising generating a graphical representation of an electroanatomic map superimposed on the interactive graphical representation of the predetermined surface region of the patient based on the electroanatomical data for the selected at least one time interval.

14. The method of claim 12, further comprising applying an inverse method to compute the electroanatomical data for the predetermined surface region based on patient electrical data acquired for the patient via non-invasive body surface electrodes and patient geometry data acquired for the patient.

15. The method of claim 14, wherein the computed electroanatomical data corresponds to simultaneous electrical activity that is time indexed over the selected at least one time interval for each of the plurality of points distributed across the predetermined surface region of the patient.

16. The method of claim 15, wherein the predetermined surface region of the patient comprises a surface of the patient's heart.

17. The method of claim 11, further comprising computing the electroanatomical data for the predetermined surface region of the patient based on patient electrical data collected from electrodes disposed on at least one electrophysiology catheter while in vivo within the patient relative to a corresponding surface of the patient's organ.

18. The method of claim 1, wherein the predetermined surface region comprises a three-dimensional surface of an organ of the patient, and
wherein the representation of physiological data further comprises a representation of physiological information spatially visualized on a graphical representation of the organ.

19. The method of claim 18, wherein the location data that defines the anatomical position for the representation of the at least one virtual electrode is received in response to selecting the anatomical position on a model of the organ via a graphical user interface element.

20. The method of claim 19, wherein the graphical user interface element comprises a graphical representation of the at least one virtual electrode.

21. The method of claim 1, further comprising:
selecting the user-selected location as at least one region of interest comprising a plurality of points on the graphical representation of the predetermined surface region of the patient; and
computing statistical information based on the electroanatomic data for plurality of points in the selected at least one region of interest.

22. A system for visualizing physiological data relative to an organ of a patient, the system comprising:
electroanatomic data for the patient stored in memory;
a patient geometry model stored as patient geometry data in the memory, the patient geometry data representing at least one surface region of the organ of the patient;
computer readable instructions stored in the memory, the computer readable instructions comprising:
a location selector programmed to generate location data as a function of a position of at least one roving virtual electrode location relative to the patient geometry model; and
an output generator that generates a visual representation of physiological data for the roving virtual electrode that is determined as a function of the location data and the electroanatomic data, the representation of physiological data for the roving virtual electrode being updated continuously responsive to changes in the current location of the roving virtual electrode as the roving virtual electrode is moved.

23. A system for visualizing physiological data for a patient, the system comprising:
means for storing electroanatomic data representing electrical activity for at least a portion of an organ of the patient;
means for storing patient geometry data that defines geometry for at least the portion of the organ;
means for providing a graphical representation of patient anatomy based on the geometry data;
means for receiving a user input corresponding to position on the graphical representation of patient anatomy, the user input varying as a function of the position of user interface pointing element, corresponding to a roving virtual electrode, and for providing corresponding location data that varies as a function of the position of the user interface pointing element as the user interface pointing element is moved relative to the graphical representation of patient anatomy;
means for computing physiological results data for the at least one user-selected location based on the location data and the electroanatomic data.

24. A computer-implemented method for visualizing physiological data of a patient, the method comprising:
storing in memory electroanatomic data representing electrical activity for a predetermined surface region of the patient;
providing an interactive graphical representation of the predetermined surface region of the patient;
assigning a configuration of at least one virtual electrode in response to a user input, the assigned configuration specifying a number of one or more electrodes and a spatial relationship for each of the one or more electrodes for the at least one virtual electrode; and
storing the assigned configuration as electrode configuration data for the at least one virtual electrode;
receiving a user input that defines location data corresponding to a user-selected location for the at least one virtual electrode on the graphical representation of the predetermined surface region of the patient; and
generating a visual representation of the physiological data for the predetermined surface region for each virtual electrode based on the location data, the electroanatomic data and the assignment data.

25. The method of claim 24, wherein the at least one virtual electrode comprises a roving virtual electrode, the method further comprising:
dynamically modifying the visual representation of the physiological data in response to changes in a current location of a roving virtual electrode corresponding to the roving virtual electrode as the roving virtual electrode is moved relative to the graphical representation of the predetermined surface region of the patient.

26. The system of claim 22, wherein the computer readable instructions further comprise:
a virtual electrode generator programmed for generating the visual representation of the roving virtual electrode in response to selecting one or more locations in the at least one surface region via a user interface pointing element, which defines the location data, the output generator dynamically modifying the visual representation of the physiological data according to changes in the location data representing an anatomical position of the roving virtual electrode relative to the graphical representation of the predetermined surface region of the patient.

* * * * *